United States Patent
Sakai et al.

(10) Patent No.: US 7,594,896 B2
(45) Date of Patent: Sep. 29, 2009

(54) WAIST CIRCUMFERENCE CALCULATION APPARATUS AND BODY COMPOSITION DETERMINATION APPARATUS

(75) Inventors: Yoshio Sakai, Shiki (JP); Hirokazu Ono, Kawasaki (JP); Koji Tsuji, Niiza (JP); Yasuhiro Kasahara, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 11/826,819

(22) Filed: Jul. 18, 2007

(65) Prior Publication Data
US 2008/0021349 A1   Jan. 24, 2008

(30) Foreign Application Priority Data
Jul. 24, 2006   (JP) ............................. 2006-201083
Feb. 5, 2007   (JP) ............................. 2007-025231

(51) Int. Cl.
*A61B 5/117*   (2006.01)
*A61B 5/103*   (2006.01)
(52) U.S. Cl. ..................................................... 600/587
(58) Field of Classification Search ................. 600/547; 33/11; 356/612, 638; 250/224, 559.22, 559.26
See application file for complete search history.

(56) References Cited

U.S. PATENT DOCUMENTS

| 4,406,544 A | 9/1983 | Takada et al. |
| 2002/0151815 A1 | 10/2002 | Kawanishi et al. |

FOREIGN PATENT DOCUMENTS

| CN | 1653980 A | 8/2005 |
| EP | 1584290 A1 | 10/2005 |
| EP | 1621131 A1 | 2/2006 |
| JP | 11-113870 | 4/1999 |
| JP | 2002219132 | 8/2002 |
| JP | 2005-187952 A | 7/2005 |
| JP | 2005-288023 | 10/2005 |
| JP | 2006-288735 | 10/2006 |
| KR | 2002-0026557 | 4/2002 |

OTHER PUBLICATIONS

Schofield et al, Defining and Testing the Assumptions used in Curretn Apparel Grading Practice, International Textile & Apparel Association, 2005 vol. 23 #3, pp. 135-150.*
Office Action issued in related Chinese Application No. 2007-10126939.2 dated May 22, 2009.

* cited by examiner

*Primary Examiner*—Max Hindenburg
*Assistant Examiner*—Brian Szmal
(74) *Attorney, Agent, or Firm*—Hogan & Hartson LLP

(57) ABSTRACT

An abdomen width determiner determines an abdomen width value of a human subject. A memory stores a correlation between abdomen width values and waist circumferences of human beings. A waist circumference calculator calculates a waist circumference of the human subject on the basis of the abdomen width value determined by the abdomen width determiner and the correlation stored in the memory. The correlation stored in the memory may be expressed by the following regression formula: $Y=aX+b$ where "Y" is a waist circumference of a human being, "X" is an abdomen width value of a human being, and "a" and "b" are constants.

16 Claims, 14 Drawing Sheets

WAIST CIRCUMFERENCE CALCULATION APPARATUS AND BODY COMPOSITION DETERMINATION APPARATUS

BACKGROUND OF THE INVENTION

1. Field of the Invention

The present invention relates to waist circumference calculation apparatuses for calculating waist circumferences of human subjects, and the present invention also relates to body composition determination apparatuses including the same.

2. Description of Prior Art

Waist circumference has been widely used as one of the indexes regarding the physique or figure of human beings in the fields of medical care, cosmetology, and health care. As lifestyle-related diseases caused by, for example, adiposity are currently receiving much attention, waist circumference is of great interest because, for example, it is used as data for diagnosis of metabolic syndrome since it is considered to be an index reflecting the amount of visceral fat.

Tape measures are generally used for measuring waist circumferences. In addition, Japanese Patent Application Publication JP-11-113870-A (published in 1999) discloses a band-type measurement apparatus that can be turned around the abdomen of a human subject in a manner similar to tape measures for measuring the waist circumference and the impedance of the abdomen.

However, it is difficult to precisely locate the tape measure or band-type apparatus at an appropriate position of the abdomen. For example, setting the tape measure at a desirable height is a very difficult and troublesome operation since the tape measure is likely to move, especially when the human subject is standing.

Furthermore, it is difficult to maintain the position of the tape measure without tightening the portion to be measured. Even if the tape measure is set at the appropriate position, tightening the measured portion causes deformation of the portion and induces measurement errors.

SUMMARY OF THE INVENTION

Accordingly, the present invention provides a waist circumference calculation apparatus that can calculate waist circumferences of human subjects in a highly reproducible manner, and a body composition determination apparatus including the waist circumference calculation apparatus.

In accordance with one aspect of the invention, there is provided a waist circumference calculation apparatus including: an abdomen width determiner for determining an abdomen width value of a human subject; a memory for storing a correlation between abdomen width values and waist circumferences of human beings; and a waist circumference calculator for calculating a waist circumference of the human subject on the basis of the abdomen width value determined by the abdomen width determiner and the correlation stored in the memory. With such a structure, the waist circumference of a human subject can be calculated with a high degree of reproducibility.

Preferably, the correlation is expressed by the following regression formula:

$$Y = aX + b$$

where "Y" is a waist circumference of a human being, "X" is an abdomen width value of a human being, and "a" and "b" are constants.

The waist circumference calculation apparatus may further include a measuring unit including at least one noncontact distance measuring sensor, the sensor emitting light, receiving the light reflected from whatever is in front of the sensor, and generating a signal corresponding to a distance from the sensor to whatever is in front of the sensor, in which the abdomen width determiner determines the abdomen width value on the basis of signals generated by the sensor. In this embodiment, the abdomen width value can be measured in a noncontact manner (e.g., without deformation of the abdomen of the human subject).

The waist circumference calculation apparatus may further include a supporting member that can be disposed in proximity to a human subject, in which the measuring unit includes at least one pair of the noncontact distance measuring sensors supported at the supporting member, the pair of the noncontact distance measuring sensors including a first sensor and a second sensor being aligned on opposite sides of the human subject within the supporting member, the first sensor measuring a first gap distance between the first sensor and a first subject position on the human subject in a first measurement line, the second sensor measuring a second gap distance between the second sensor and a second subject position on the human subject in a second measurement line parallel to or identical to the first measurement line, the measuring unit measuring a plurality of first gap distances to a plurality of first subject positions in a plurality of parallel first measurement lines and a plurality of second gap distances to a plurality of second subject positions in a plurality of parallel second measurement lines lying on a plane identical to that in which the first measurement lines lie, and the abdomen width determiner further includes: a distance calculator for calculating a plurality of candidate subject widths on the basis of the plurality of the first gap distances and second gap distances, each candidate subject width being a distance between one of the first subject positions and one of the second subject positions; and a maximum selector for selecting a maximum subject width as the abdomen width value from among the plurality of candidate subject widths.

The waist circumference calculation may further include driving mechanisms for respectively moving the first sensor and the second sensor with respect to the supporting member, in which the first sensor measures a plurality of first gap distances to a plurality of first subject positions in a plurality of first parallel measurement lines, each first gap distance being between a sensor position of the first sensor and a first subject position on the human subject, and the second sensor measures a plurality of second gap distances to a plurality of second subject positions in a plurality of second parallel measurement lines, each second gap distance being between a sensor position of the second sensor and a second subject position on the human subject. In this embodiment, each sensor can measure a plurality of gap distances.

In an embodiment, the measuring unit includes a plurality of pairs of the noncontact distance measuring sensors, each pair including the first sensor and the second sensor fixedly supported at the supporting member, in which each of the first sensors measures a first gap distance between the corresponding first sensor and a first subject position on the human subject in a first measurement line, each of the second sensors measures a second gap distance between the corresponding second sensor and a second subject position on the human subject in a second measurement line parallel to or identical to the first measurement line. In this embodiment, the apparatus can be manufactured easily since the sensors are fixed to the supporting member.

The waist circumference calculation apparatus may further include a supporting member that can be disposed in proximity to a human subject, in which the at least one noncontact distance measuring sensor is supported at the supporting member, the measuring unit measuring a plurality of gap distances between the sensor and a plurality of measured positions in a plurality of measurement lines parallel to an anteroposterior direction of the human subject, and the abdomen width determiner may further include: an end detector for detecting a first end and a second end of the human subject on the basis of an amount of each of the plurality of gap distances; and a distance calculator for calculating a distance between the first end and the second end as the abdomen width value.

The waist circumference calculation apparatus may further include a driving mechanism for moving the sensor with respect to the supporting member, in which the sensor measures a plurality of gap distances to a plurality of measured positions in a plurality of parallel measurement lines. In this embodiment, a single sensor can measure a plurality of gap distances.

In an embodiment, the measuring unit includes a plurality of the sensors fixedly supported at the supporting member for measuring a plurality of gap distances to a plurality of measured positions in a plurality of parallel measurement lines, respectively. In this embodiment, the apparatus can be manufactured easily since the sensors are fixed to the supporting member.

In an embodiment, the supporting member has a recess being of a curved shape that can fit over an anterior surface of the abdomen of the human subject. In this embodiment, deformation of the abdomen of the human subject can be reduced.

The waist circumference calculation apparatus may further include a navel position indicator disposed at the supporting member for indicating a reference position at which a navel of the human subject would be located. In this embodiment, deployment, i.e., positioning of the apparatus can be assisted.

In an embodiment, the supporting member is a frame having a shape in which one side is open, and the supporting member can be disposed around the human subject. Since one side of the supporting member is open, the apparatus can be located around the human subject easily. This feature is especially advantageous when measurements are taken of an elderly bed-ridden person or a physically disabled person.

The waist circumference calculation apparatus may further include a rod for supporting the supporting member so that the supporting member can slide along a medial line of a human subject. In this embodiment, the position of the apparatus along the medial line of the human subject can be adjusted easily.

In accordance with another aspect of the invention, there is a body composition determination apparatus including: a waist circumference calculation apparatus according to above-described embodiments of the invention; a bioelectrical impedance measuring unit for measuring a bioelectrical impedance of the abdomen of the human subject; and a body composition calculator for calculating an index of a body composition of the human subject on the basis of the waist circumference calculated by the waist circumference calculation apparatus and the bioelectrical impedance measured by the bioelectrical impedance measuring unit. Since the waist circumference calculation apparatus of the above-described embodiments can precisely calculate the waist circumference, the body composition determination apparatus can determine the precise index of the body composition on the basis of the waist circumference.

BRIEF DESCRIPTION OF THE DRAWINGS

With reference to the accompanying drawings, various embodiments of the present invention will be described hereinafter. In the drawings.

DETAILED DESCRIPTION OF PREFERRED EMBODIMENTS

First Embodiment

A body composition determination apparatus according to a first embodiment of the present invention includes a waist circumference calculation apparatus. The waist circumference calculation apparatus measures abdomen width values of a human subject lying down, and calculates the waist circumference of the subject on the basis of a previously stored correlation between abdomen width values and waist circumferences of human beings. The correlation is expressed by a formula determined on the basis of statistics on the relationship between waist circumferences of human beings measured using CT (computerized axial tomography) and abdomen width values of human beings. The body composition determination apparatus further includes an abdomen bioelectrical impedance measuring unit for measuring a bioelectrical impedance (bioimpedance) of the abdomen of the human subject, and determines body composition indexes on the basis of the calculated waist circumference and the measured bioelectrical impedance.

Figure 1:
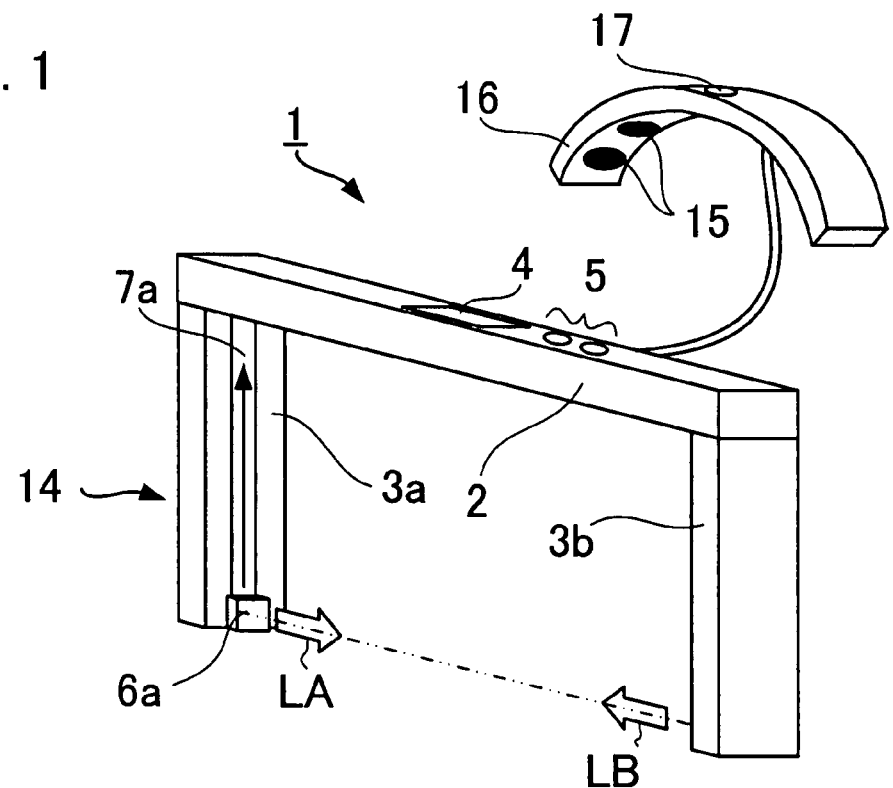
FIG. 1 is a perspective view of a body composition determination apparatus according to a first embodiment of the invention.
Figure 2:
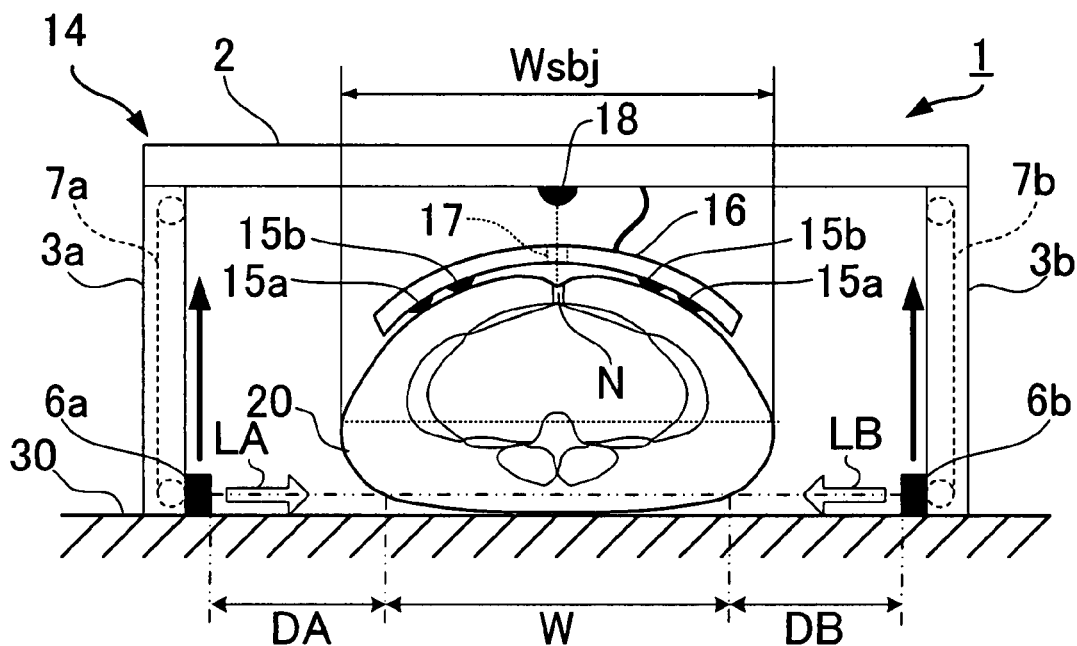
FIG. 2 is a front view of the body composition determination apparatus in FIG. 1, which has been set with respect to a human subject.
Figure 3:
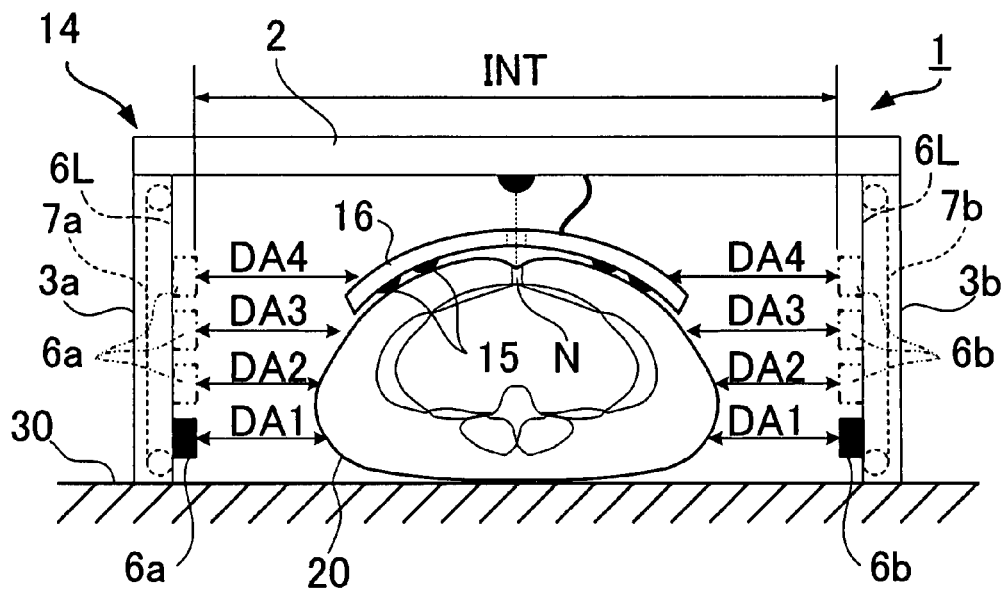
FIG. 3 is a front view of the body composition determination apparatus in FIG. 1, which is measuring distances.

As shown in FIGS. 1 through 3, the body composition determination apparatus according to this embodiment includes a portable supporting member 14. The supporting member 14 is a frame of a generally rectangular shape in which one side is open. More specifically, the supporting member 14 has a pair of parallel legs 3a and 3b vertically standing on a floor or bed 30, and a connection part 2 of which both ends are connected to the legs 3a and 3b. As shown in FIGS. 2 and 3, the body composition determination apparatus 1 is disposed so that the connection part 2 is opposed to the anterior surface of the abdomen of the human subject 20 on the bed 30, with the subject lying on the subject's back. By virtue of the open side of the supporting member 14, the apparatus 1 can be easily located around the human subject. This feature is especially advantageous when the human subject 20 is an elderly bed-ridden person or a physically disabled person.

A console of the body composition determination apparatus 1 is provided at the connection part 2. The console includes a display 4 for displaying operation guidance, measurement results, or other information for the operator, and a manual interface 5 including at least one of buttons and switches by which the operator can provide commands to the apparatus for, for example, turning on power or starting measurement. Inside the connection part 2, an electrical circuit, which will be described later, is provided for controlling the body composition determination apparatus 1.

The body composition determination apparatus 1 includes a bioelectrical impedance measuring unit for measuring a bioelectrical impedance of the abdomen of the human subject 20. As shown in FIG. 1, the bioelectrical impedance measuring unit includes electrodes 15 for measuring the bioelectrical impedance of the human subject 20, and electrode supporting part 16 for supporting the electrodes 15 so that the electrodes 15 can be in contact with the anterior surface of the abdomen of the human subject 20. The electrodes 15 are arranged on the electrode supporting part 16 in a manner known to those skilled in the art. More specifically, as shown in FIG. 2, the electrodes 15 includes a pair of voltage measurement electrodes 15a and a pair of current supplying electrodes 15b disposed between the pair of voltage measurement electrodes 15a. The electrodes 15 are electrically connected to the electrical circuit within the connection part 2. The bioelectrical impedance is determined on the basis of the current passing between the current supplying electrodes 15b through the human subject 20, and the potential difference between the voltage measurement electrodes 15a. More specifically, it is the ratio of the potential difference between the voltage measurement electrodes 15a to the current passing between the current supplying electrodes 15b.

The electrode supporting part 16 has a through hole 17 at its center. Before measurement of the bioelectrical impedance, as shown in FIG. 2, the electrode supporting part 16 is disposed on the anterior surface of the abdomen so that a navel N of the human subject 20 can be seen through the through hole 17. Thus, the electrodes 15 can be located at predetermined parts of the abdomen of the human subject 20 by using the navel N as a reference position.

As shown in FIGS. 2 and 3, the body composition determination apparatus 1 includes a navel position indicator 18 (not shown in FIG. 1) for indicating a reference position at which the navel N of the human subject 20 would be located. The navel position indicator 18 is disposed at the center between the legs 3a and 3b on the connection part 2. In this embodiment, the navel position indicator 18 is, but is not limited to, a light emitter for emitting reference light (e.g., a laser pointer that emits a narrow beam) onto the human subject 20. The supporting member 14 is disposed over the human subject 20 so that the navel N of the human subject 20 is located at the reference position indicated by the navel position indicator 18 (so that the reference light is emitted onto the navel N). The electrode supporting part 16 is disposed on the human subject 20 so that the reference light emitted from the navel position indicator 18 passes through the through hole 17. Positioning of the supporting member 14 with respect to the human subject 20 in this manner enables precise measurement of the abdomen width value without errors caused by mispositioning.

The body composition determination apparatus 1 also includes a measuring unit for measuring a plurality of widths W, shown in FIG. 2, of the abdomen of the human subject 20. The measuring unit includes a pair of noncontact distance measuring sensors, that is, a first sensor 6a and a second sensor 6b supported on the legs 3a and 3b of the supporting member 14, respectively. The first sensor 6a and the second sensor 6b are aligned on opposite sides of the human subject 20 within the supporting member 14. Each sensor is an optical distance sensor that has a light emitter for emitting horizontally a light beam (such as, for example, but not limited to, an infrared light beam) and a light receiver for receiving the light reflected from whatever is in front of the sensor, such as the human subject 20, and for generating a signal corresponding to the distance from the corresponding sensor to whatever is in front of the sensor. Thus, each sensor measures the gap distance between the corresponding sensor and whatever is in front of the sensor.

In FIGS. 1 and 2, arrows LA and LB represent the light beams horizontally emitted from the sensors 6a and 6b. In the state shown in FIG. 2, the first sensor 6a measures a first gap distance DA between the first sensor 6a and a first subject position on the human subject 20 with which a first horizontal measurement line (path of the light beam from the sensor 6a) intersects, and the second sensor 6b measures a second gap distance DB between the second sensor 6b and a second subject position on the human subject 20 with which a second horizontal measurement line (path of the light beam from the sensor 6b) intersects. As shown in FIGS. 1 and 2, the first and second measurement lines are identical.

Driving mechanisms 7a and 7b are respectively located at the legs 3a and 3b for respectively moving the first and second noncontact distance measuring sensors 6a and 6b to an extent vertically with respect to the frame 14. For example, each driving mechanism includes an endless belt trained over pulleys driven by rotation means, e.g., a stepping motor, and the corresponding sensor 6a or 6b is attached to the endless belt. Other suitable driving mechanisms, known to those skilled in the art, may also be used. By means of the driving mechanisms 7a and 7b, the first sensor 6a and the second sensor 6b are raised and lowered synchronously along the legs 3a and 3b in the same vertical plane, as depicted by phantom lines in FIG. 3.

During the period in which the first sensor 6a is moved vertically, the first sensor 6a measures a plurality of first gap distances DA1 through DA4 to a plurality of first (left) subject positions in a plurality of first parallel horizontal measurement lines on the same vertical plane, each first gap distance being between a sensor position of the first sensor 6a and a first (left) subject position on the human subject 20. While the second sensor 6b is moved vertically, the second sensor 6b measures a plurality of second gap distances DB1 through DB4 to a plurality of second (right) subject positions in a plurality of second parallel horizontal measurement lines on the same vertical plane identical to that in which the first measurement lines lie, each second gap distance being between a sensor position of the second sensor 6b and a second (right) subject position on the human subject 29. Therefore, although the measuring unit has only two sensors, each single sensor can measure a plurality of gap distances to a plurality of subject positions on the human subject 20 in a plurality of parallel horizontal lines. In FIG. 3, the first gap distances DA1 through DA4 and the second gap distances DB1 through DB4 are shown as examples; however, it is to be understood that the number of gap distances is not limited to that in the embodiment as shown.

Although the sensors 6a and 6b are moved, the horizontal distance-interval INT between them in a horizontal direction that is parallel to the first and second measurement lines remains unchanged since the supporting legs 3a and 3b are parallel. Thus, on the basis of the plurality of first gap distances DA and second gap distances DB and the constant interval INT, it is possible to estimate a plurality of candidate subject widths W that are candidates for the abdomen width value Wsbj (i.e., the maximum among the candidate subject widths W). For example, when the gap distances DA1 and DB1 are at the same elevation, a candidate subject width is equal to INT minus DA1 minus DB1. Similarly, another candidate subject width is equal to INT minus DA2 minus DB2. A third candidate subject width is equal to INT minus DA3 minus DB3, whereas a fourth candidate subject width is equal to INT minus DA4 minus DB4. As will be understood from FIG. 3, each candidate subject width W is a distance between one of the first (left) subject positions and one of the second (right) subject positions.

The real abdomen width value is nearly equal to the maximum among the above-mentioned plurality of candidate subject widths W. The precision of estimation of the abdomen width value Wsbj will be improved when the vertical distance-interval of the horizontal measurement lines is reduced and the number of measured gap distances is increased.

Figure 4:
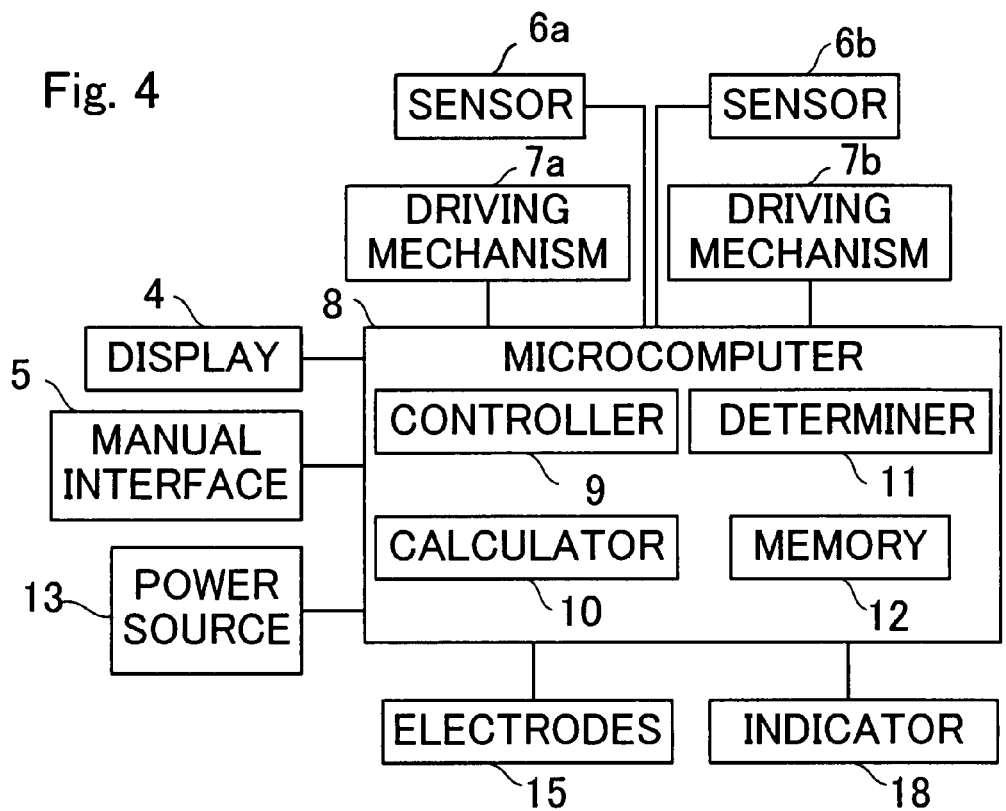
FIG. 4 is a block diagram showing elements of the body composition determination apparatus in FIG. 1.

With reference to the block diagram of FIG. 4, the electrical structure of the body composition determination apparatus 1 will be described. The above-mentioned electrical circuit within the connection part 2 includes a microcomputer 8 that is connected with the display 4, the manual interface 5, the sensors 6a and 6b, the driving mechanisms 7a and 7b, the electrodes 15, and the navel position indicator 18. The microcomputer 8 is actuated by a power source 13 and includes a memory 12 and a processor including a controller 9, a calculator 10, and a determiner 11. The controller 9, the calculator 10, and the determiner 11 are functionally realized by software.

The controller 9, i.e., the control means, conducts overall control of the body composition determination apparatus 1. The overall control includes control of the sensors 6a and 6b for measuring the gap distances DA and DB and control of the driving mechanisms 7a and 7b for moving the sensors 6a and 6b.

The calculator 10 serves as a distance calculator, i.e., distance calculating means for calculating the plurality of candidate subject widths W on the basis of the plurality of first gap distances DA and second gap distances DB measured by the sensors 6a and 6b.

The determiner 11 serves as a maximum selector, i.e., maximum selecting means, for selecting the maximum from among the plurality of candidate subject widths W as the abdomen width value of the human subject 20. Thus, the distance calculator (calculator 10) and the maximum selector (determiner 11) cooperate to serve as an abdomen width determiner for determining the abdomen width value Wsbj of the human subject 20.

The determiner 11 also serves as a limit detector, i.e., limit detecting means, for determining whether or not at least one of the first sensor 6a and the second sensor 6b has reached a limit of movement of the corresponding sensor. In this embodiment, the determiner 11 conducts such limit detection for each of the sensors 6a and 6b. If the determiner 11 has detected that a sensor has reached the limit of movement, the controller 9 serves as a measurement terminator, i.e., measurement terminating means, for terminating the corresponding sensor measuring the corresponding gap distance.

The memory 12 stores in advance various data such as default values, system settings, and arithmetic expressions. The abdomen width value Wsbj determined by the determiner 11 is also stored in the memory 12.

Furthermore, the memory 12 stores the above-mentioned correlation between abdomen width values and waist circumferences of human beings. The calculator 10 serves as not only the distance calculator, but also a waist circumference calculator, i.e., waist circumference calculating means, for calculating the waist circumference of the human subject 20 corresponding to the determined abdomen width Wsbj on the basis of the correlation stored in memory 12.

Figure 5:
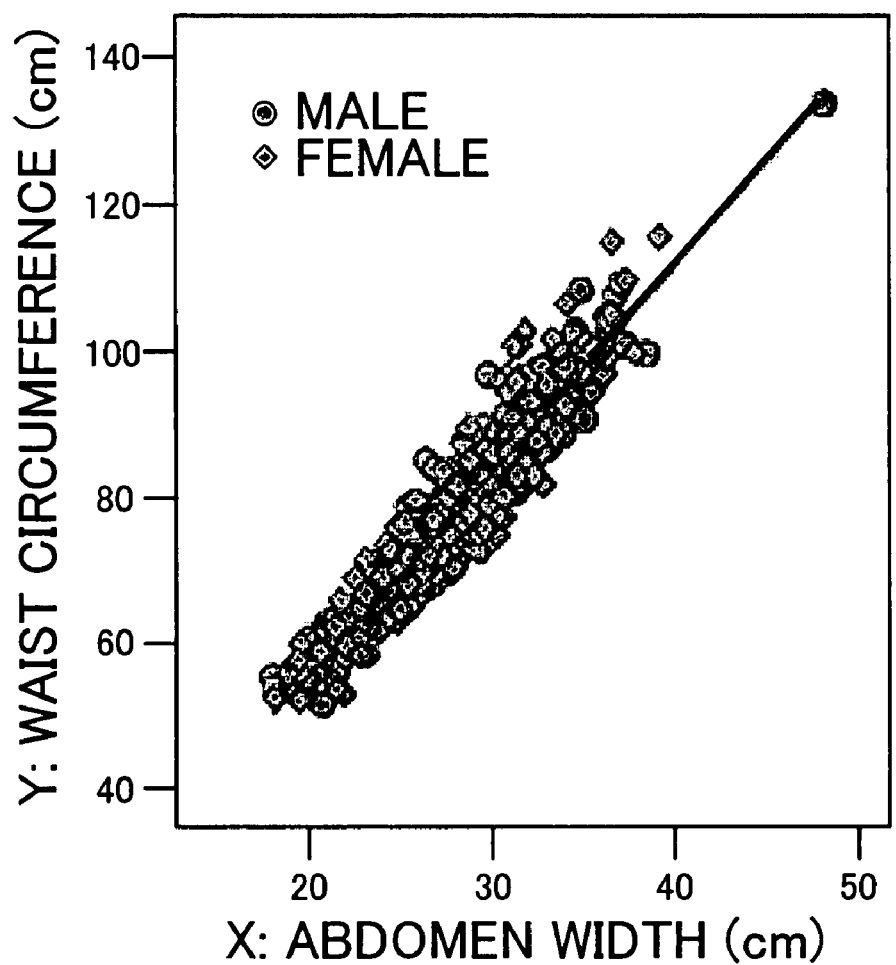
FIG. 5 is a graph showing the statistical correlation between abdomen width values and waist circumferences of human beings.

The correlation is statistically estimated in advance from among measured data of a plurality of human subjects. The correlation is, for example, expressed by a regression formula determined on the basis of measurement results, depicted in FIG. 5, of abdomen width values and waist circumferences measured with CT of a plurality of human beings, but it is not limited thereto. The following is an exemplary regression formula representing the straight line shown in FIG. 5.

$Y=aX+b$ where "Y" is a waist circumference of a human being, "X" is an abdomen width of a human being, and "a" and "b" are constants. The constants "a" and "b" are preferably, 3.01 and −10.2, respectively, but they are not limited thereto. The constant "a" is preferably greater than 2.3 and less than 3.14, and the constant "b" is selected depending upon the constant "a". For example, the constant "a" may be 2.49 and the constant "b" may be 10.5.

In addition, the memory 12 stores body composition index formulae for calculating various body composition indexes of human subjects on the basis of the bioelectrical impedance and the waist circumference. The calculator 10 further serves as a body composition calculator, i.e., body composition calculating means, for calculating body composition indexes of the human subject 20, on the basis of the body composition index formulae, corresponding to the bioelectrical impedance measured with the electrodes 15 and the waist circumference calculated by the waist circumference calculator. The body composition index formulae may be, for example, formulae known in the art for calculating indexes of visceral fat as body composition indexes.

The controller 9, the calculator 10, and the determiner 11 may be realized physically by a plurality of central processing units. Alternatively, they may be realized functionally by a computer program that is executed by a single central processing unit.

Figure 6:
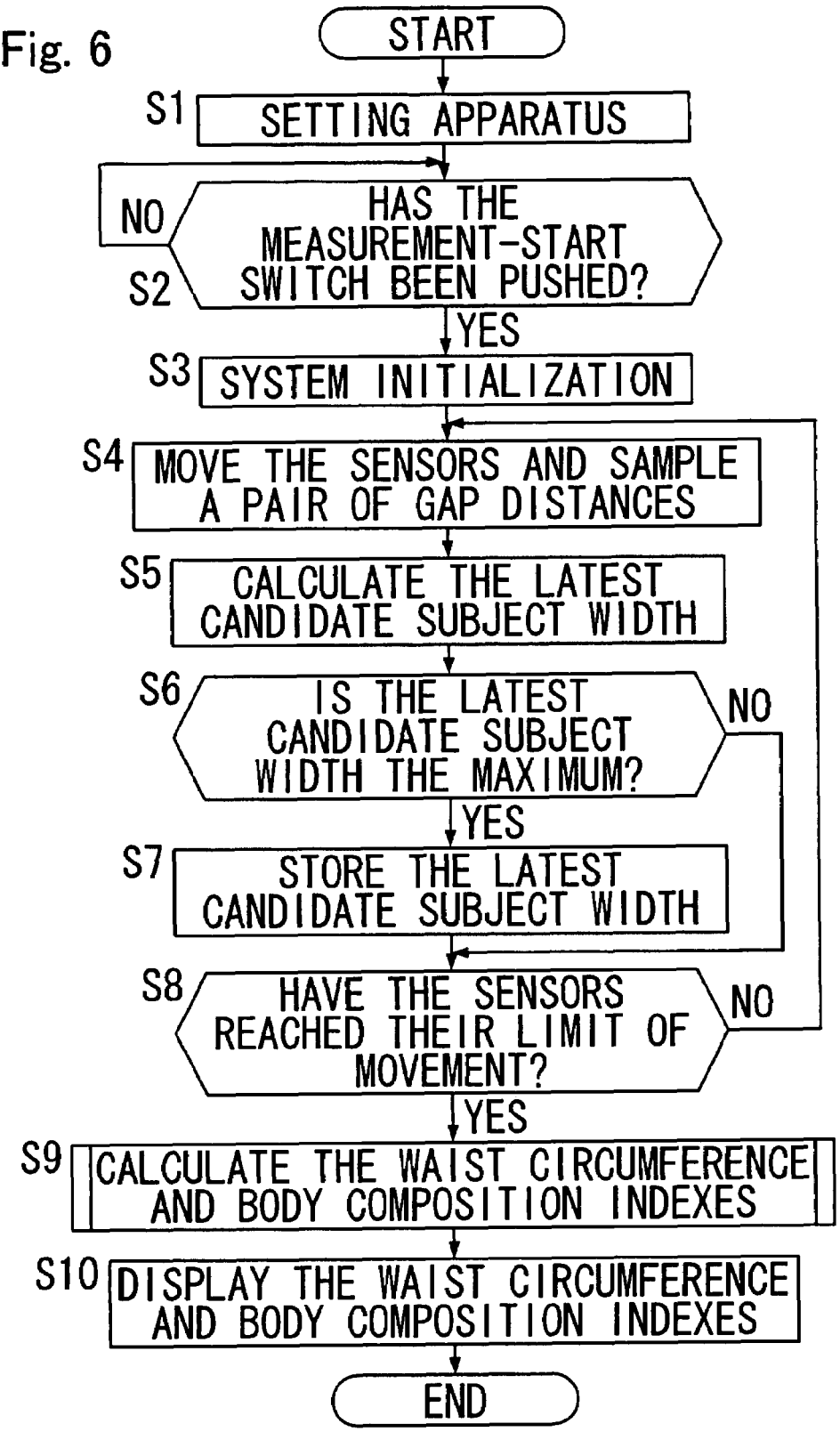
FIG. 6 is a flowchart showing use and operations of the body composition determination apparatus in FIG. 1.

With reference to the flowchart shown in FIG. 6, use and operations of the body composition determination apparatus 1 will be described in more detail. The memory 12 permanently stores a computer program for controlling the body composition determination apparatus 1. The microcomputer 8 operates according to the computer program. Steps executed by the microcomputer 8 within the operations in the flowchart correspond to the computer program or an element of the computer program. In this embodiment, the memory 12 is used as a storage medium for storing the computer program or program element, but another memory or storage device may be used as such a storage medium. A semiconductor memory, hard disc, compact disc, digital versatile disc, flexible disc, or other suitable storage medium may be used for this purpose.

After manipulation of the power switch of the manual interface 5 for turning on power, the operator sets the body composition determination apparatus 1 on the bed 30 in such a manner that the frame 14 lies over the human subject 20 at step S1. The following operations are steps executed by the microcomputer 8 according to the program.

At step S2, the microcomputer 8 determines whether or not the measurement-start switch of the manual interface 5 has been pushed. If so, the process proceeds to step S3 where the microcomputer 8 initializes the entire system. For example, the microcomputer 8 initializes the positions of the sensors 6a and 6b and data in the memory 12.

After system initialization, at step S4, the microcomputer 8 serves as the controller 9 to control the driving mechanisms 7a and 7b for moving the sensors 6a and 6b synchronously, and serves to activate the sensors 6a and 6b for measuring (sampling) one pair of the first gap distance DA and the second gap distance DB.

As will be understood from the flowchart, whenever the process returns to step S4, the sensors 6a and 6b are moved synchronously and activated to measure the next pair of first gap distance and second gap distance, so that the human subject 20 is scanned at regular sampling time intervals. Each of the driving mechanisms 7a and 7b under the control of the controller 9 moves the sensors 6a and 6b at the same speed, so that the sensors 6a and 6b are kept at the same elevation during such movement and measurement. The sampling period-interval multiplied by the movement speed of the sensors 6a and 6b is the sampling distance-interval (distance-interval of the horizontal measurement lines). For example, when the sampling distance-interval is one millimeter and the sampling period-interval is 50 milliseconds, the speed would be 0.02 meters per second.

At step S5, the microcomputer 8 serves as the calculator 10 for calculating the latest candidate subject width W on the basis of the above-mentioned horizontal distance-interval INT and the pair of first gap distance DA and second gap distance DB measured at the last time by the sensors 6a and 6b.

At step S6, the microcomputer 8 serves as the determiner 11 for determining whether or not the latest candidate subject width W is the current maximum in the measured cross section. In this embodiment, the value of the current maximum subject width is stored in the memory 12, and the determiner 11 determines whether or not the latest candidate subject width W is greater than the current maximum subject width that has been stored in the memory 12. The default value of the maximum subject width in the memory 12 is zero.

If the latest candidate subject width W is greater, the process proceeds to step S7 where the determiner 11 erases the maximum subject width stored previously in the memory 12 and stores in the memory 12 the latest candidate subject width W as the new maximum subject width. That is, the determiner 11 renews the maximum subject width in the memory 12. Then, the process proceeds to step S8. In contrast, if the latest candidate subject width W is not greater, the process proceeds to step S8 directly without renewing the maximum subject width in the memory 12.

At step S8, the microcomputer 8 serves as the determiner 11 for determining whether or not the first sensor 6a and the second sensor 6b have reached their limit 6L of movement (see FIG. 3). For example, a time period necessary for the sensors 6a and 6b to reach the limit 6L of movement is calculated on the basis of the traveling speed of the sensors 6a and 6b and the length from the start position and the limit 6L of movement. The necessary time period is stored in the memory 12, and the microcomputer 8 has a timer for counting elapsed time since the start of travel of the sensors 6a and 6b. When the elapsed time has reached the necessary time period, the determiner 11 determines that the sensors have reached the limit 6L.

If the sensors have not reached the limit 6L, the process returns to step S4 where the next first gap distance and the next second gap distance are measured. If the sensors have reached the limit 6L, the process proceeds to step S9. The maximum subject width stored last in the memory 12 is fixed as the abdomen width value Wsbj. At step S9, the microcomputer 8 executes a subroutine for calculating the waist circumference and body composition indexes of the human subject 20. Then, the microcomputer 8 acts as a display controller at step S10 for making the display 4 show the value of the waist circumference and body composition indexes calculated at step S9. The microcomputer 8 controls the display 4 such that the display holds the displayed waist circumference and body composition indexes for a period of time. Since the display holds the displayed values at least temporarily, the operator can easily confirm the displayed value after completion of measurement, and it is possible to avoid change of the displayed image even if the sensors are moved accidentally after completion of measurement. After step S10, the process ends.

Figure 7:
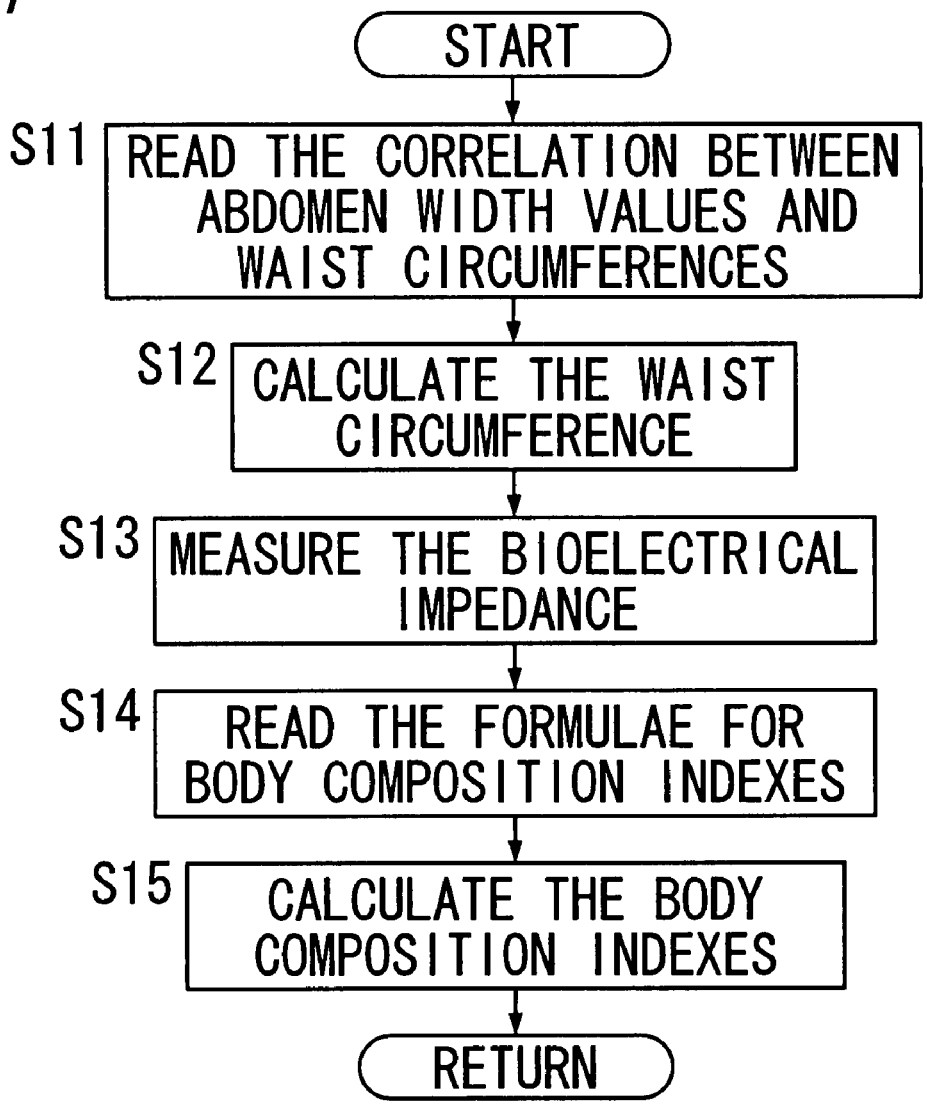
FIG. 7 is a flowchart showing operations of the body composition determination apparatus at step S9 in FIG. 6.

With reference to the flowchart shown in FIG. 7, operations of the body composition determination apparatus 1 at step S9 shown in FIG. 6 will be described in more detail. The microcomputer 8 reads the regression formula representing the correlation between abdomen width values and waist circumferences from the memory 12 at step S11.

At step S12, the microcomputer 8 serves as the calculator 10 (waist circumference calculator) for calculating the waist circumference Y of the human subject 20 on the basis of the regression formula and the determined abdomen width.

At step S13, the microcomputer 8 measures the bioelectrical impedance on the basis of the signals supplied from the electrodes 15 in a manner known in the art. Then, at step S14, the microcomputer 8 reads the body composition index formulae for calculating the body composition indexes. At step S15, the microcomputer 8 serves as the calculator 10 for calculating the body composition indexes (e.g., index about visceral fat) of the human subject 20 corresponding to the measured bioelectrical impedance and the calculated waist circumference on the basis of the body composition index formulae. The body composition indexes may be calculated in a manner disclosed in Japanese Patent Application Publication JP-2006-288735-A (published in 2006). The disclosure of which is herein incorporated by reference in its entirety. The body composition indexes include, for example, but are not limited to, subcutaneous fat area, subcutaneous fat thickness, total fat area of the abdomen, visceral fat area, fat ratio of trunk portion, fat ratio of the entire body, and abdominal muscle thickness. After calculation of the body composition indexes, the process proceeds to step S10 in the main routine shown in FIG. 6.

The above-described body composition determination apparatus 1 calculates the body composition indexes on the basis of the waist circumference of the human subject 20. However, the body composition indexes may be calculated on the basis of the abdomen width value of the human subject 20 measured by the measuring unit (sensors 6a and 6b) as disclosed in Japanese Patent Application Publication JP-2005-288023-A (published in 2005). The disclosure of which is herein incorporated by reference in its entirety.

In the above-described first embodiment, the driving mechanisms 7a and 7b are driven synchronously to move the sensors 6a and 6b simultaneously. However, the present invention is not intended to be limited to this embodiment. In an alternative embodiment, the controller 9 may drive the driving mechanisms 7a and 7b separately to move the sensors 6a and 6b at different times, but the sampling distance-interval and the sampling start elevation for the sensor 6a may be the same as those for the sensor 6b, so that the first parallel horizontal measurement lines of the sensor 6a coincide with the second parallel horizontal measurement lines of the sensor 6b. The microcomputer 8 may store all of the measured first gap distances DA and the second gap distances DB consecutively in the memory 12. In this alternative embodiment, the calculator 10 may calculate all of the candidate subject widths W consecutively on the basis of the first gap distances DA and the second gap distances DB stored in the memory 12, in which each candidate subject width W is calculated on the basis of the above-mentioned horizontal distance-interval INT and first gap distance DA and second gap distance DB on the same elevation, and the determiner 11 may select the maximum from among all of the calculated candidates as the abdomen width value Wsbj.

Second Embodiment

With reference to FIGS. 8 through 14, a waist circumference calculation apparatus 101 according to a second embodiment of the present invention will be described. The apparatus 101 does not measure the bioelectrical impedance or calculate of the body composition indexes differently from the body composition determination apparatus 1 according to the first embodiment.

Figure 8:
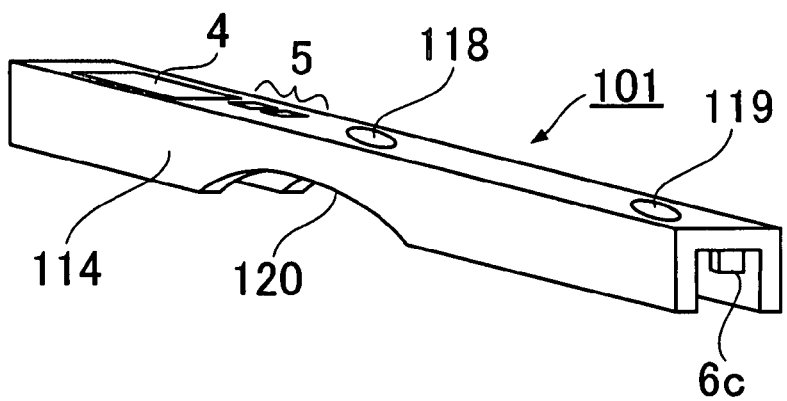
FIG. 8 is a perspective view of a waist circumference calculation apparatus according to a second embodiment of the invention.
Figure 9:
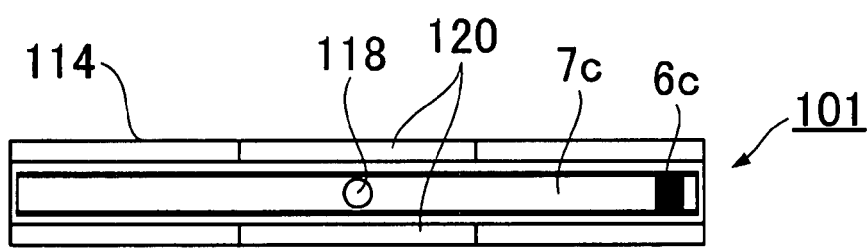
FIG. 9 is a bottom view of the waist circumference calculation apparatus in FIG. 8.
Figure 10:
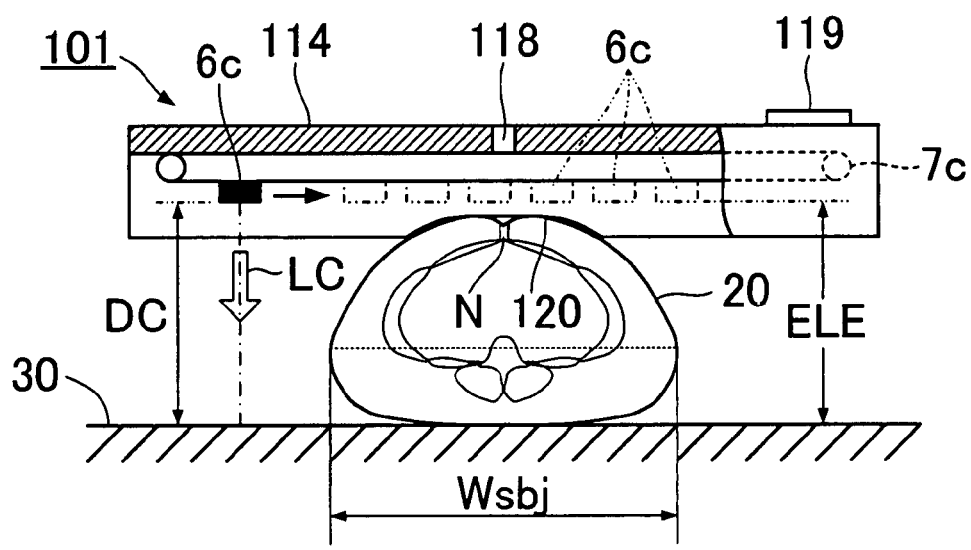
FIG. 10 is a front view of the waist circumference calculation apparatus in FIG. 8, which has been set with respect to the human subject.
Figure 11:
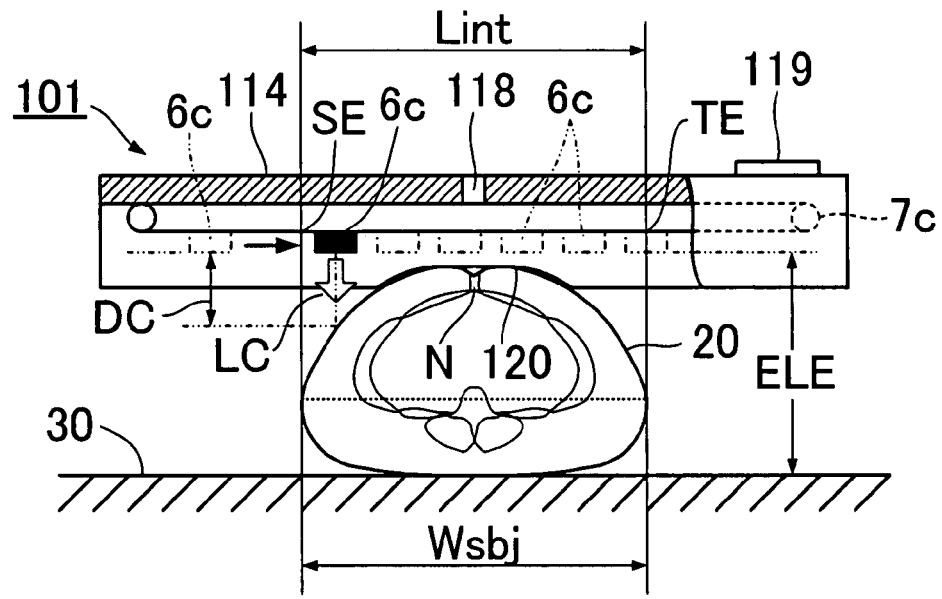
FIG. 11 is a front view of the waist circumference calculation apparatus in FIG. 8, which is in a situation different from that in FIG. 10.

As shown in FIGS. 8 through 11, the waist circumference calculation apparatus 101 includes a portable supporting member 114 instead of the supporting member 14 in the first embodiment. As shown in FIGS. 10 and 11, the supporting member 114 is horizontally disposed on the anterior surface of the human subject 20. The supporting member 114 is provided with a level adjustment-assisting unit 119 (e.g., a level meter or an angle sensor) for assisting the operator in adjusting the supporting member 114 to be horizontal (i.e., to be parallel to the surface of the floor or the bed 30).

The supporting member 114 has a contact part 120. The contact part 120 is a recess of a curved shape that can fit over the anterior surface of the abdomen of the human subject 20. The contact part 120 enables the supporting member 114 (the waist circumference calculation apparatus 101) to be located on the anterior surface with stability. In addition, by virtue of the contact part 120, change of relative positions of the supporting member 114 and the human subject 20 is reduced. Although placing the supporting member 114 may cause deformation of the anterior surface, the effect of the abdomen deformation on waist circumference is smaller than that caused by breathing in the inventors' experience. Thus, precise measurement of the waist circumference with a high degree of reproducibility is achieved, even though the supporting member 114 is disposed directly on the abdomen.

Furthermore, the supporting member 114 has a navel position indicator 118 for indicating a reference position at which the navel N of the human subject 20 would be located. The navel position indicator 118 is, but is not limited to, a through hole formed at the center of the supporting member 114. The supporting member 114 is positioned with respect to the human subject 20 so that the navel N can be seen through the navel position indicator 118. Positioning the supporting member 114 in this manner enables a precise measurement of the abdomen width value Wsbj without errors caused by mispositioning. Thus, the navel position indicator 118, the level adjustment-assisting unit 119, and the contact part 120 assist the operator in precisely locating the waist circumference calculation apparatus 101 at a position at which it can measure the waist circumference with a high level of reproducibility, the position being on a circumference on which the navel N is located.

The waist circumference calculation apparatus 101 also includes a measuring unit for measuring the abdomen width value Wsbj shown in FIG. 10. The measuring unit of this embodiment includes a single noncontact distance measuring sensor 6c movably supported at the supporting member 114. The type of sensor employed is the same as that in the first embodiment. Thus, the sensor 6c has a light emitter for emitting a light beam (such as, for example, but not limited to, an infrared light beam) downward in a direction perpendicular to the surface of the floor or bed 30, and a light receiver for receiving the light reflected from whatever is in front of the sensor 6c, such as the human subject 20 or the bed 30, and for generating a signal corresponding to the distance from the sensor 6c to whatever is in front of the sensor 6c. Thus, the sensor 6c measures the gap distance between the sensor 6c and a measured position in a measurement line extending vertically. In FIGS. 10 and 11, arrow LC represents the light beam downwardly emitted from the sensor 6c.

As shown in FIG. 9, a driving mechanism 7c is disposed at the supporting member 114 for moving the sensor 6c to an extent with respect to the supporting member 114. The type of the driving mechanism employed is the same as that in the first embodiment. By means of the driving mechanism 7c, the sensor 6c is shifted horizontally along the supporting member 114 (i.e., in a direction parallel to the floor or bed 30), as depicted by phantom lines in FIGS. 10 and 11.

During the period in which the sensor 6c is moved horizontally, the single sensor 6c measures a plurality of gap distances DC to a plurality of measured, positions in a plurality of parallel vertical measurement lines on the same vertical plane, each gap distance being between a sensor position of the sensor 6c and a measured position on the bed 30 or the human subject 20.

In the state shown in FIG. 10, the sensor 6c measures a gap distance DC between the sensor 6c and the bed 30 with which a vertical measurement line (path of the light beam from the sensor 6c) intersects. The gap distance DC in this state is almost equal to a reference elevation ELE of the sensor 6c that is the vertical distance between the sensor 6c and the bottom of the legs 3a and 3b. On the other hand, in the state shown in FIG. 11, the sensor 6c measures another gap distance DC between the sensor 6c and a subject position of the human subject 20 with which another vertical measurement line (path of the light beam from the sensor 6c) intersects.

As will be understood from FIG. 10, the gap distance DC measured is very large when the sensor 6c is not located above the human subject 20. In contrast, as shown in FIG. 11, the gap distance DC measured is small when the sensor 6c is located above the human subject 20. Therefore, both ends SE and TE of the human subject 20 can be detected on the basis of comparison of the size of the gap distance DC with at least one threshold, and the abdomen width value Wsbj of the human subject 20 between both ends SE and TE of the human subject 20 can be estimated. This is a generic principle of the abdomen width measurement achieved by the apparatus 101. The precision of estimation of the abdomen width value Wsbj will be improved when the horizontal distance-interval of the vertical measurement lines is reduced and the number of measured gap distances is increased.

Figure 12:
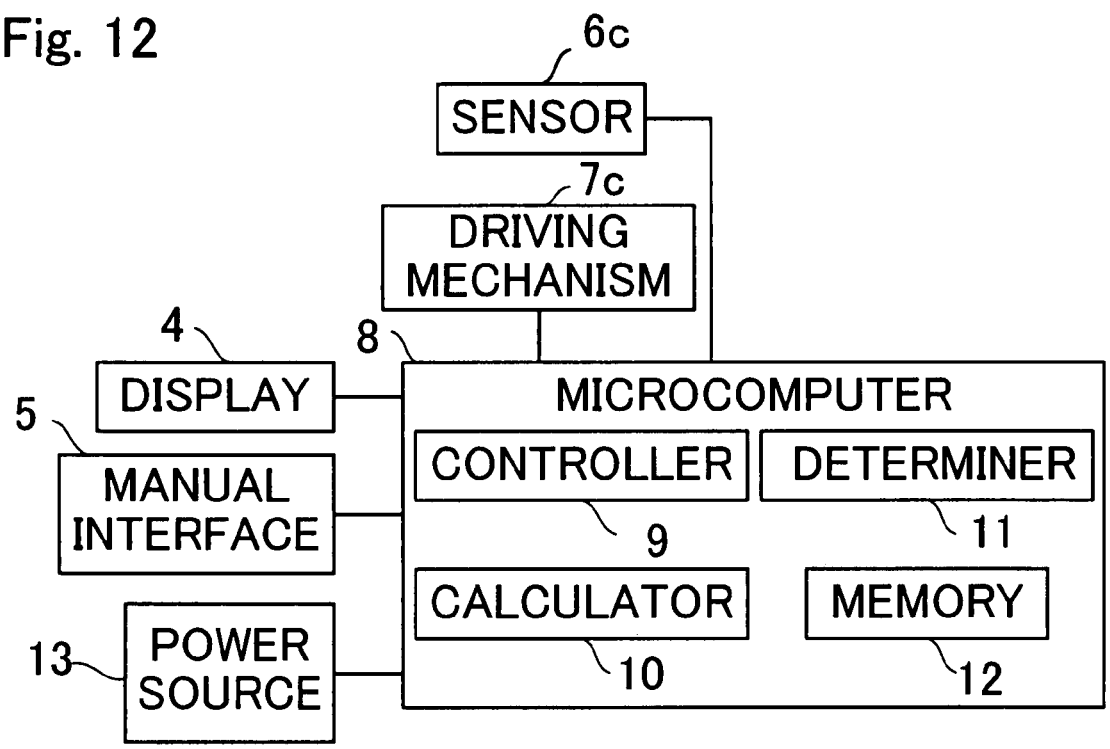
FIG. 12 is a block diagram showing elements of the waist circumference calculation apparatus in FIG. 8.

With reference to the block diagram of FIG. 12, the electrical structure of waist circumference calculation apparatus 101 will be described. The block diagram of FIG. 12 is similar to FIG. 4 of the first embodiment, but in FIG. 12, the sensor 6c and the driving mechanism 7c are electrically connected with the microcomputer 8 instead of the sensors 6a and 6b and the driving mechanisms 7a and 7b. Additionally, the electrodes 15 and the navel position indicator 18 are not used.

Instead of control of the sensors 6a and 6b for distance measurement and the driving mechanisms 7a and 7b for moving the sensors 6a and 6b, the controller 9 controls the sensor 6c for measuring the distances DC and controls the driving mechanism 7c for moving the sensor 6c.

The calculator 10 serves as a distance calculator, i.e., distance calculating means for calculating the abdomen width value Wsbj between both ends, namely the first and second ends of the human subject 20.

The determiner 11 serves as an end detector, i.e., end detecting means for detecting the first end and the second end of the human subject 20 on the basis of an amount of each of the plurality of gap distances DC.

The memory 12 stores in advance various data such as default values, system settings, and arithmetic expressions. For example, the memory 12 of this embodiment stores in advance thresholds for determining the first end SE and the second end TE of the human subject 20. Furthermore, the memory 12 stores in advance the correlation between abdomen width values and waist circumferences described above in conjunction with FIG. 5. As described in the first embodiment, the correlation is expressed by the following regression formula:

$$Y=aX+b$$

Figure 13A:
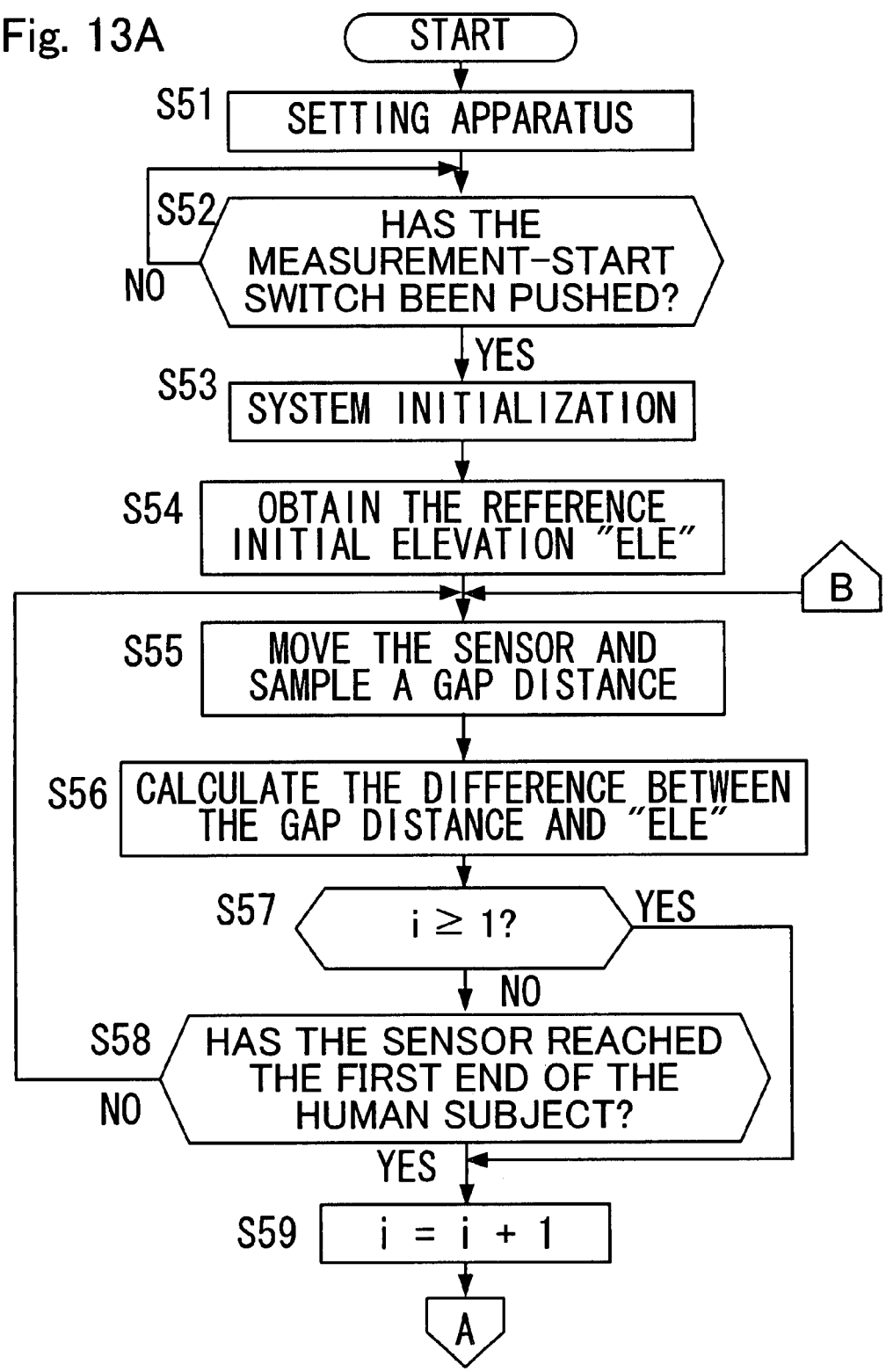
FIGS. 13A and 13B form a flowchart showing use and operations of the waist circumference calculation apparatus in FIG. 8.
Figure 13B:
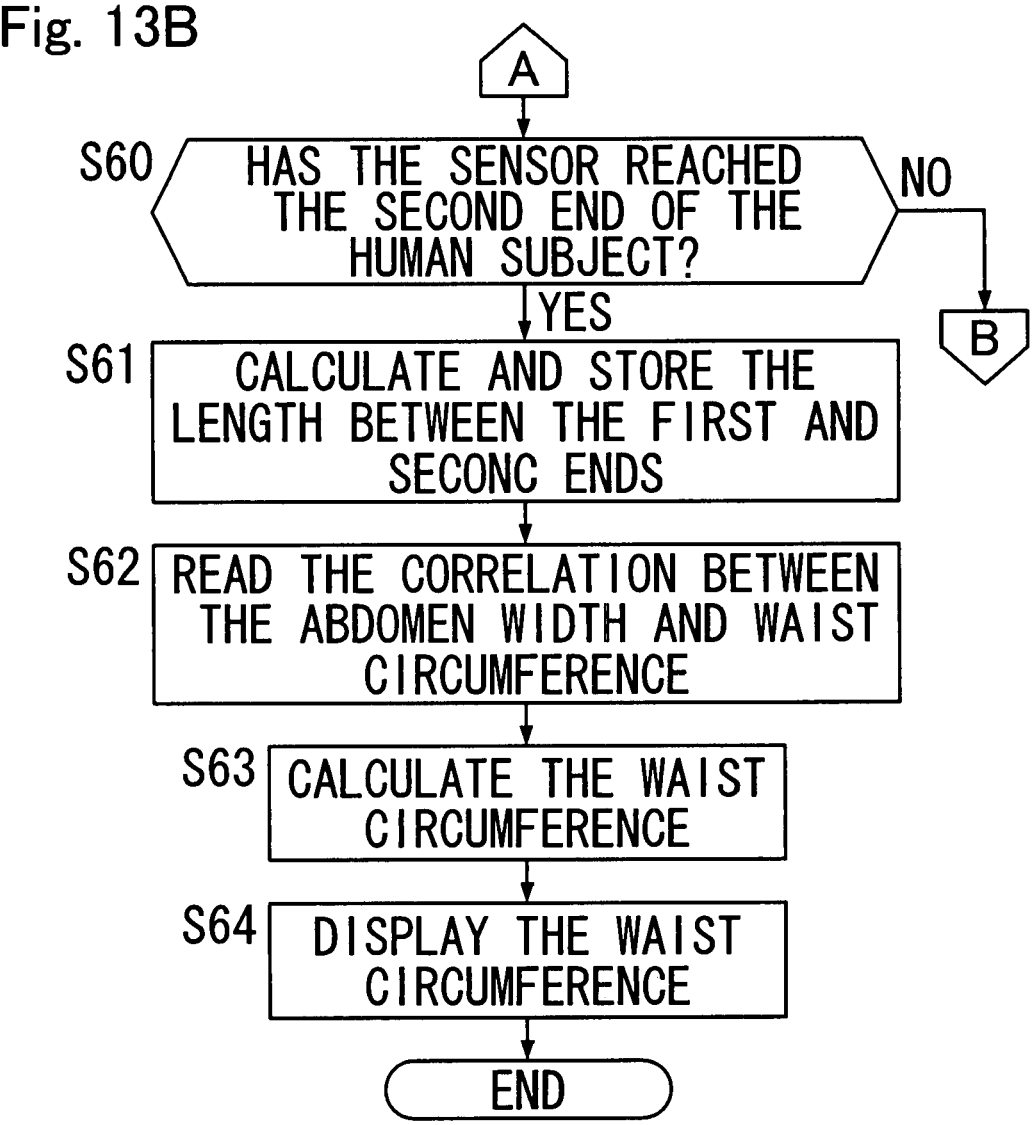

With reference to the flowchart shown in FIGS. 13A and 13B, use and operations of the waist circumference calculation apparatus 101 will be described in more detail. Steps executed by the microcomputer 8 within the operations in the flowchart correspond to the computer program or an element of the computer program stored in the memory 12 or another memory or storage device. Steps S51, S52, and S53 after turning on power are the same as steps S1, S2, and S3 in FIG. 6 of the first embodiment, and they are therefore not described in detail. However, at step S53, the microcomputer 8 initializes the position of the sensor 6c instead of the positions of the sensors 6a and 6b. In addition, a counter is functionally or physically provided in the microcomputer 8 for counting the number of times of sampling of gap distances DC when the sensor 6c is located above the human subject 20. The counter number "i" is reset at zero (default value) at step S53 for system initialization.

At step S54, the microcomputer 8 serves as the controller 9 to activate sensor 6c, and therefore, the sensor 6c measures the initial vertical gap distance between the sensor 6c and the bed 30. The microcomputer 8 thus obtains this initial vertical gap distance and stores it as a reference initial elevation ELE of the sensor 6c in the memory 12.

At step S55, the microcomputer 8 serves as the controller 9 to control the driving mechanism 7c for moving the sensor 6c at a constant speed. As a result, the sensor 6c measures (samples) one of the gap distances DC. As will be understood from the flowchart, whenever the process returns to step S55, the sensor 6c is moved and activated to measure the next gap distance DC, so that the human subject 20 is scanned at regular sampling time intervals.

At step S56, the calculator 10 calculates the difference between the last measured gap distance and the reference initial elevation ELE. At step S57, the microcomputer 8 serves as the determiner 11 for determining whether or not the vertical measurement line of the sensor 6c is located above the human subject 20. This determination is achieved by determining whether or not the above-mentioned counter number "i" is equal to or greater than one.

If "i" is less than one (the sensor 6c is not above the human subject 20), the process proceeds to step S58 where the determiner 11 serves as the end detector for determining whether or not the measurement line of the sensor 6c has reached the first end (start end) SE of the human subject 20. This determination is achieved by comparing the difference calculated at step S56 with a threshold P stored in the memory 12. If the difference is greater than P, the measurement line of the sensor 6c has reached the start end SE. This determination is the same as that in which the determiner 11 determines that the sensor 6c has reached the start end SE of the human subject 20 when the sensor 6c measures a gap distance DC that is less than another threshold.

If the determination at step S58 is negative (the difference is not greater than P), the process returns to step S55 where the next gap distance DC is sampled. If the determination at step S58 is affirmative (the difference is greater than P), the process proceeds to step S59 where the microcomputer 8 increments the counter number "i" by one.

If the counter number "i" is equal to or greater than one, the determination at step S57 is affirmative and the process proceeds directly to step S59 (not via step S58) since the system already knows that the sensor 6c is traveling above the human subject 20.

At step S60, the determiner 11 serves as the end detector for determining whether or not the measurement line of the sensor 6c has reached the second end (termination end) TE of the human subject 20. This determination is achieved by comparing the difference calculated at step S56 with a threshold Q stored in the memory 12. The threshold Q may be or may be not the same as the above-mentioned threshold P. If the difference is equal to or less than Q, the measurement line of the sensor 6c has reached the termination end TE. This determination is the same as that in which the determiner 11 determines that the sensor 6c has reached the termination end TE of the human subject 20 when the sensor 6c measures a gap distance DC that is greater than another threshold.

If the determination at step S60 is negative (the difference is greater than Q), the process returns to step S55 where the next gap distance DC is sampled since the sensor 6c is still traveling above the human subject 20.

If the determination at step S60 is affirmative (the difference is not greater than Q), the process proceeds to step S61 where the controller 9 serves as a measurement terminator, i.e., measurement terminating means and terminates the sensor 6c measuring the gap distance and the driving mechanism 7c moving the sensor 6c. Furthermore, the microcomputer 8 holds the current number "i" of the sampling counter, and then on the basis of this number, the calculator 10 serves as the distance calculator and calculates an interval length Lint (in FIG. 11) between the sensor position at which the first end SE is detected and the sensor position at which the second end TE is detected. The interval length Lint equals the abdomen width value Wsbj between the first end SE and the second end TE. The calculation of the interval length Lint is achieved by multiplying the sampling distance-interval by the counter number "i", in which the sampling distance-interval is the sampling period-interval multiplied by the traveling speed of the sensor 6c. The calculator 10 stores the abdomen width value Wsbj (Lint) in the memory 12.

At step S62, the microcomputer 8 reads the above-described regression formula (i.e., the correlation between abdomen width values and waist circumferences) from the memory 12.

At step S63, the microcomputer 8 serves as the calculator 10 (waist circumference calculator) for calculating the waist circumference Y of the human subject 20 on the basis of the regression formula and the calculated abdomen width value Wsbj (X in the regression formula) of the human subject 20. The calculator 10 stores the waist circumference Y in the memory 12. At step S64, the microcomputer 8 acts as a display controller for making the display 4 show the waist circumference stored in the memory 12. After step S64, the process for calculating the waist circumference ends.

In the above-described second embodiment, the supporting member 114 of a rod shape is illustrated. However, the shape of the supporting member 114 is not limited to this. For example, a frame which is generally rectangular shape in which one side is open, similar to the supporting member 14 in the first embodiment, may be employed instead of the supporting member 114 in the second embodiment.

In the above-described second embodiment, the interval length Lint is calculated on the basis of the sampling counter number "i". However, it is not intended to limit the present invention to this embodiment. In an alternative embodiment, a distance encoder (not shown) may be incorporated in the driving mechanism 7c for measuring the interval length Lint. The distance encoder starts measuring the length when the determiner 11 informs the encoder that the sensor 6c has reached the first end SE. The distance encoder terminates measuring the length Lint when the determiner 11 informs the encoder that the sensor 6c has reached the second end TE.

The above-mentioned initial vertical gap distance need not necessarily be measured in practice since the reference initial elevation ELE is the vertical distance between the sensor 6c and the bottom of the legs 3a and 3b. Therefore, the reference initial elevation ELE may be stored in the memory 12 in advance.

In the above-described second embodiment, the first and second ends are determined on the basis of the gap distances DC measured. However, in an alternative embodiment, the determiner 11 (end detector) may determine that the sensor 6c has reached the first end SE when the sensor 6c outputs an error signal, and may determine that the sensor 6c has reached the second end TE when the sensor 6c outputs an error signal again. This alternative embodiment is advantageous in a situation in which there is no suitable reference horizontal plane, to which the initial vertical gap distance can be measured from the sensor, at each side of the human subject 20 within the movable range of the sensor 6c. In accordance with the alternative embodiment, the reference initial elevation ELE and the thresholds can be excluded from use.

In another alternative embodiment (not shown), the sensor 6c may be moved manually by the operator, with respect to the frame 14, while the sensor samples the gap distances DC at regular sampling distance intervals.

Figure 14:
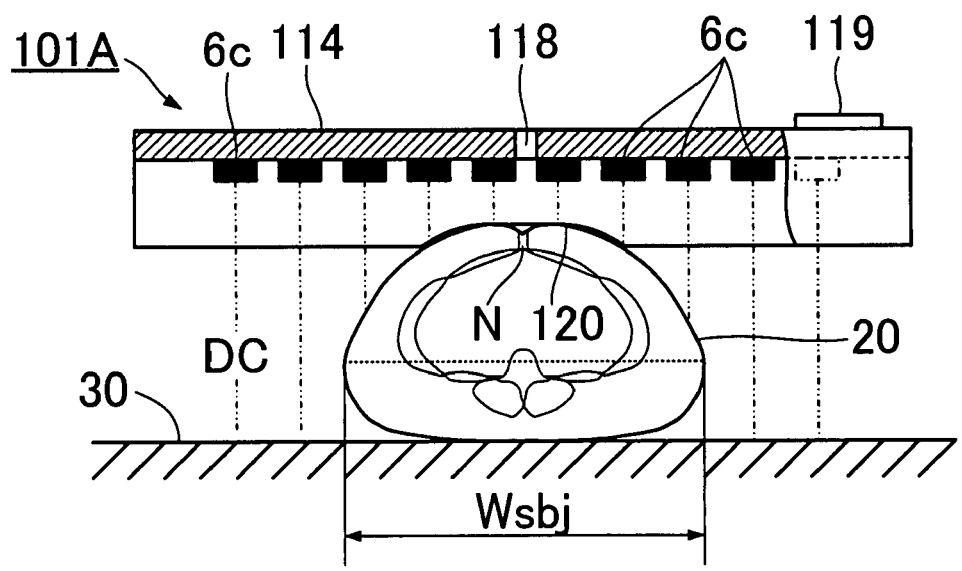
FIG. 14 is a front view of a waist circumference calculation apparatus according to a modification of the second embodiment, which has been set with respect to a human subject.

In another alternative embodiment shown in FIG. 14, the measuring unit of a waist circumference calculation apparatus 101A includes a plurality of the noncontact distance measuring sensors 6c fixedly supported at the supporting member 114. The sensors 6c are spaced equally with respect to each other and measure a plurality of gap distances DC to a plurality of measured positions in a plurality of vertical parallel measurement lines, respectively. In this embodiment, the apparatus can be manufactured easily since the sensors 6a are fixed to the supporting member 114 and the above-described driving mechanism 7c is excluded. In addition, the use of the apparatus is simplified since the automatic or manual movement of the sensor 6c is unnecessary. The precision of estimation of the abdomen width value Wsbj will be improved when the number of the sensors is increased.

Third Embodiment

With reference to FIGS. 15 through 19, a waist circumference calculation apparatus 201 according to a third embodiment of the present invention will be described. The waist circumference calculation apparatus 201 calculates the waist circumference of the standing human subject 20 and does not measure the bioelectrical impedance or calculate the body composition indexes differently from the first embodiment.

Figure 15:
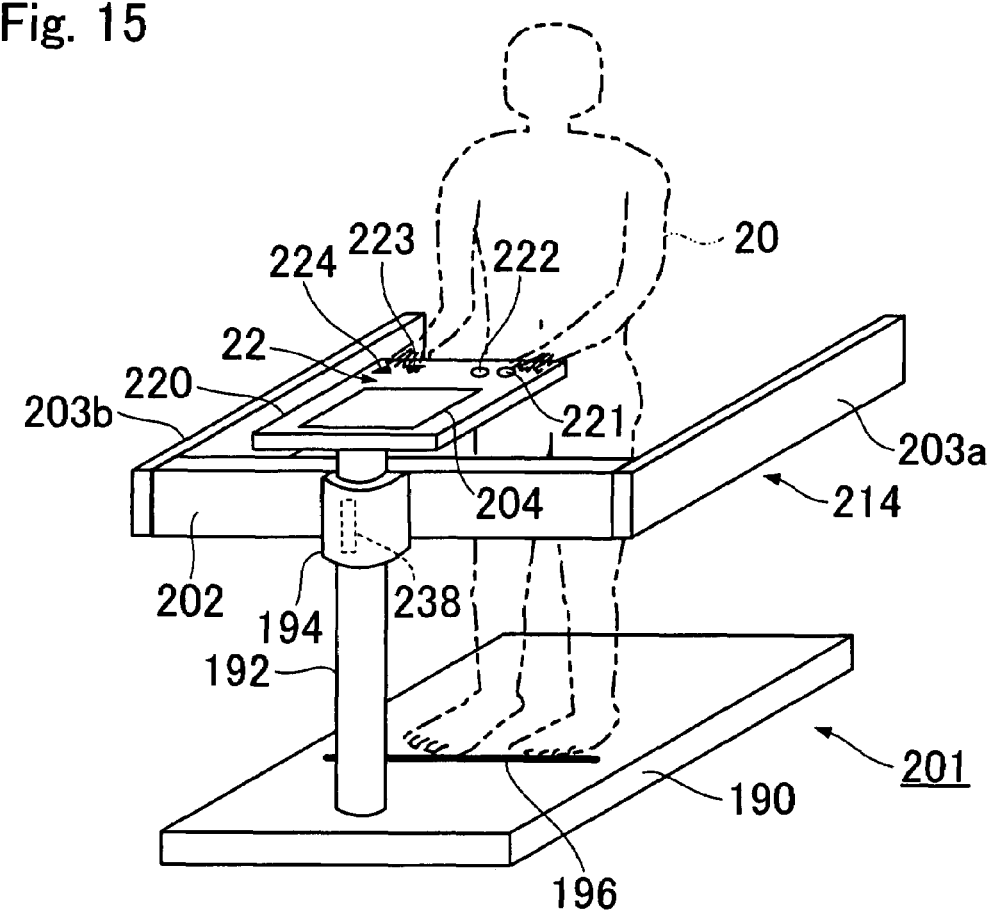
FIG. 15 is a perspective view of a waist circumference calculation apparatus according to a third embodiment of the invention.

As shown in FIG. 15, the waist circumference calculation apparatus 201 includes a base plate 190 on which the human subject 20 stands, a rod (i.e., pillar) 192 vertically erected on the base plate 190, and a supporting member 214 supported by the rod 192. On the top surface of the base plate 190, a reference line 196 is drawn on which the toes of the human subject 20 should be aligned.

The supporting member 214 has a pair of parallel arms 203a and 203b extending horizontally, and a connection part 202 of which both ends are connected to the arms 203a and 203b. Since the supporting member 214 is a frame of generally rectangular shape in which one side is open, the supporting member 214 can be easily disposed around the human subject 20 (i.e., the human subject 20 can easily enter the interior area defined by the supporting member 214). Thus, the supporting member 214 in this embodiment enables easy and speedy measurement.

The supporting member 214 further includes an attachment part 194 disposed around the rod 192 for attaching the supporting member 214 to the rod 192. Inside the attachment part 194, a driving unit (i.e., driving means) 238 is disposed for moving the supporting member 214 vertically with respect to the rod 192. For example, the driving unit 238 includes a moving part (e.g., a ball screw or an endless belt) and a driving mechanism (e.g., a motor) for driving the moving part. Thus, the supporting member 214 can automatically slide along the medial line of the standing human subject 20.

As shown in FIG. 15, a console 220 is disposed at the top end of the rod 192. The console 220 includes a manual interface 22 as the input device on its top surface. The human subject 20 or another operator can provide commands to the waist circumference calculation apparatus 201 by manipulating the manual interface 22. The manual interface 22 includes an ON/OFF key 221, a Fix key 222, a Move-up key 223, and a Move-down key 224. In addition, the console 220 includes a display 204 for displaying operation guidance, measurement results, or other information for the operator.

Figure 16:
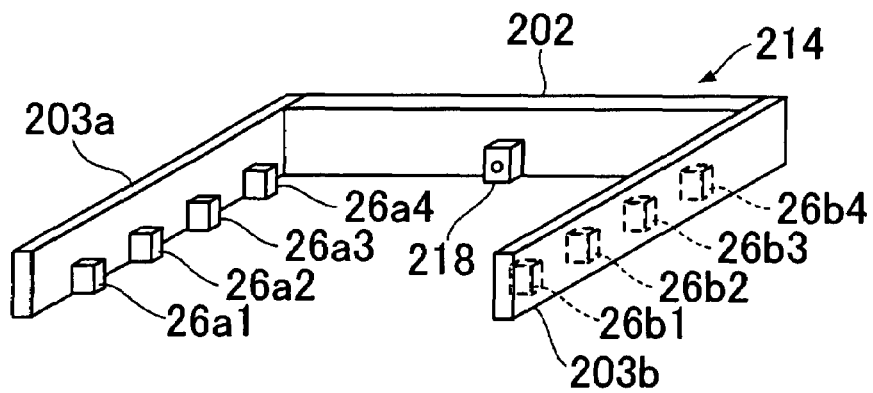
FIG. 16 is a perspective view of a supporting member of the waist circumference calculation apparatus in FIG. 15.
Figure 17:
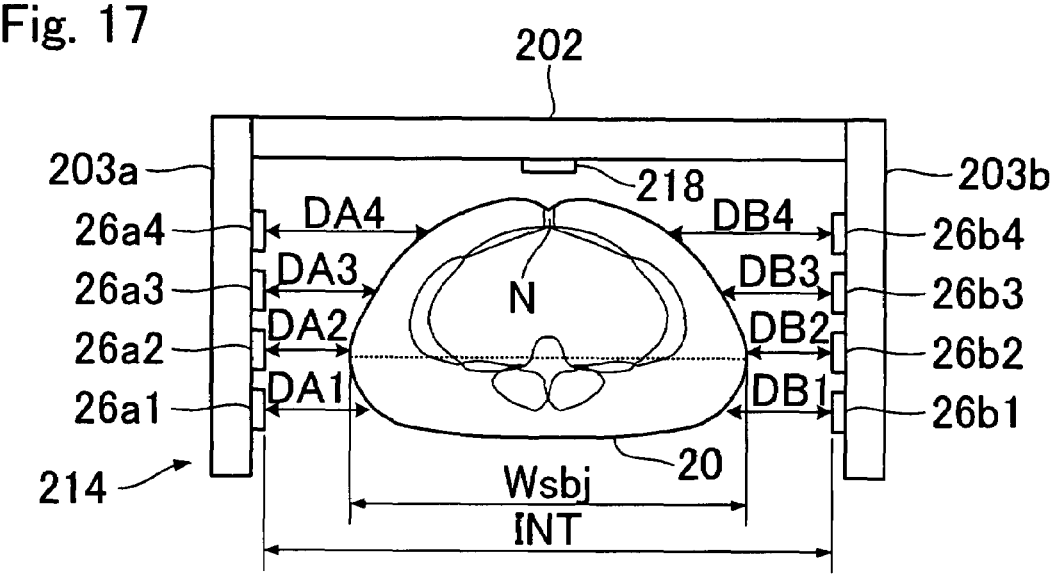
FIG. 17 is a top view of the supporting member of FIG. 16 which the human subject has entered.

The waist circumference calculation apparatus 201 includes a measuring unit for measuring the abdomen width value Wsbj in FIG. 17. As shown in FIGS. 16 and 17, the measuring unit of this embodiment includes a plurality of pairs (four pairs) of noncontact distance measuring sensors 26 disposed in the same horizontal plane. Each pair includes a first sensor 26a and a second sensor 26b. The type of sensors employed is the same as that in the first embodiment. The number of the pairs of sensors is not limited to that in the illustrated embodiment.

The first sensors 26a (26a1 through 26a4) are fixedly supported at the arm 203a and are aligned at regular distance intervals in the anteroposterior direction of the human subject 20. Similarly, the second sensors 26b (26b1 through 26b4) are fixedly supported at the arm 203b and are aligned at regular distance intervals in the anteroposterior direction. As shown in FIG. 17, the first sensors 26a and the second sensors 26b are aligned on opposite sides of the abdomen of the human subject 20 within the supporting member 214. Thus, the first sensors 26a and the second sensors 26b are disposed symmetrically with respect to an anteroposterior line of the human subject 20. That is, the first sensor 26a and the second sensor 26b of the same pair are located in the same horizontal line parallel to a lateral direction of the human subject 20. The distance between the first sensors 26a and the second sensor 26b is INT in FIG. 17.

Each of the first sensors 26a1 through 26a4 measures a first gap distance DA (one of DA1 through DA4) between the corresponding first sensor and a first subject position on the human subject 20 with which a first horizontal measurement line (path of the light beam from the sensor 26a) intersects. The first sensors 26a1 through 26a4 generate and output signals corresponding to the first gap distances DA1 through DA4, respectively. Each of the second sensors 26b1 through 26b4 measures a second gap distance DB (one of DB1 through DB4) between the corresponding second sensor and a second subject position on the human subject 20 with which a second horizontal measurement line (path of the light beam from the sensor 6b) intersects. The second sensors 26b1 through 26b4 generate and output signals corresponding to the second gap distances DB1 through DB4, respectively. The second measurement lines and the first measurement lines are parallel to a lateral direction of the human subject 20 standing on the base plate 190.

As shown in FIGS. 16 and 17, the waist circumference calculation apparatus 201 includes a navel position indicator (i.e., navel position indicating means) 218. The navel position indicator 218 is disposed at the center between the arms 203a and 203b on the connection part 202 in the horizontal plane on which the sensors 26 (26a, 26b) are located. Similarly to the navel position indicator 18 of the first embodiment, the navel position indicator 218 is, for example, but is not limited to, a light emitter for emitting reference light (e.g., a laser pointer that emits a narrow beam) onto the human subject 20. The height of the supporting member 214 with respect to the human subject 20 is adjusted so that the navel N of the human subject 20 is located at the reference position indicated by the navel position indicator 218 (so that the reference light is emitted onto the navel N). Positioning of the supporting member 214 with respect to the human subject 20 in this manner enables a precise measurement of the abdomen width value without errors caused by mispositioning.

Figure 18:
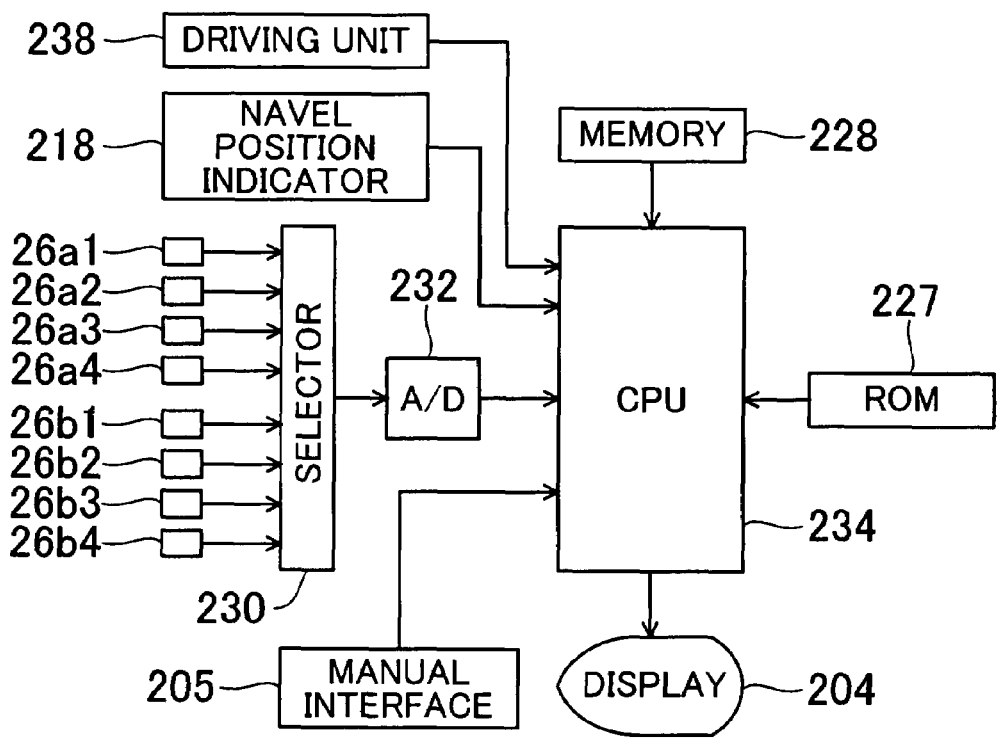
FIG. 18 is a block diagram showing elements of the waist circumference calculation apparatus in FIG. 15.

Inside the console 220, an electrical circuit is provided for controlling the waist circumference calculation apparatus 201. As shown in FIG. 18, the electrical circuit includes a selector 230, an A/D (analog-to-digital) converter 232, a CPU (central processing unit) 234, a ROM (read-only memory) 227, and a memory 228. The selector 230 outputs the signals from the sensors 26 to the A/D converter 232 one by one in sequence. The A/D converter 232 converts the signal supplied from the selector 230 into a digital signal. The digital signal is supplied to the CPU 234. Thus, the digital signals corresponding to the output signals from the sensors 26 are supplied to the CPU 234. Each of the digital signals represents the gap distance (DA or DB) between the corresponding sensor 26 and the subject position on the human subject 20. The CPU 234 stores the distance data represented by the digital signals in the memory 228. The memory 228 is, for example, but is not limited to, a volatile storage device and is used by the CPU 234 as a work area.

The CPU 234 serves as a controller (i.e., control means) for controlling the driving unit 238, the navel position indicator 218 and the display 204 by executing a computer program or an element of the computer program stored in the ROM 227. In addition, the CPU 234 conducts operations corresponding to signals supplied from the manual interface 205 including the above-described ON/OFF key 221, the Fix key 222, the Move-up key 223, and the Move-down key 224.

The CPU 234 serves as an abdomen width determiner (i.e., abdomen width determining means) for determining the abdomen width value Wsbj in FIG. 17 on the basis of the distance data temporally stored in the memory 228. The ROM (i.e., storage means) 227 stores the correlation between abdomen width values and waist circumferences described above in conjunction with FIG. 5. The CPU 234 also serves as a waist circumference calculator (i.e., waist circumference calculating means) for calculating the waist circumference of the human subject 20 on the basis of the abdomen width value Wsbj and the correlation stored in the ROM 227.

With reference to the flowchart shown in FIG. 19, operations of the waist circumference calculation apparatus 201 will be described in more detail. The ROM 227 stores the computer program or program element corresponding to the flowchart. In this embodiment, the ROM 227 is used as a storage medium for storing the computer program or program element, but another memory or storage device may be used as such a storage medium. A semiconductor memory, hard disc, compact disc, digital versatile disc, flexible disc, or other suitable storage medium may be used for this purpose.

Figure 19:
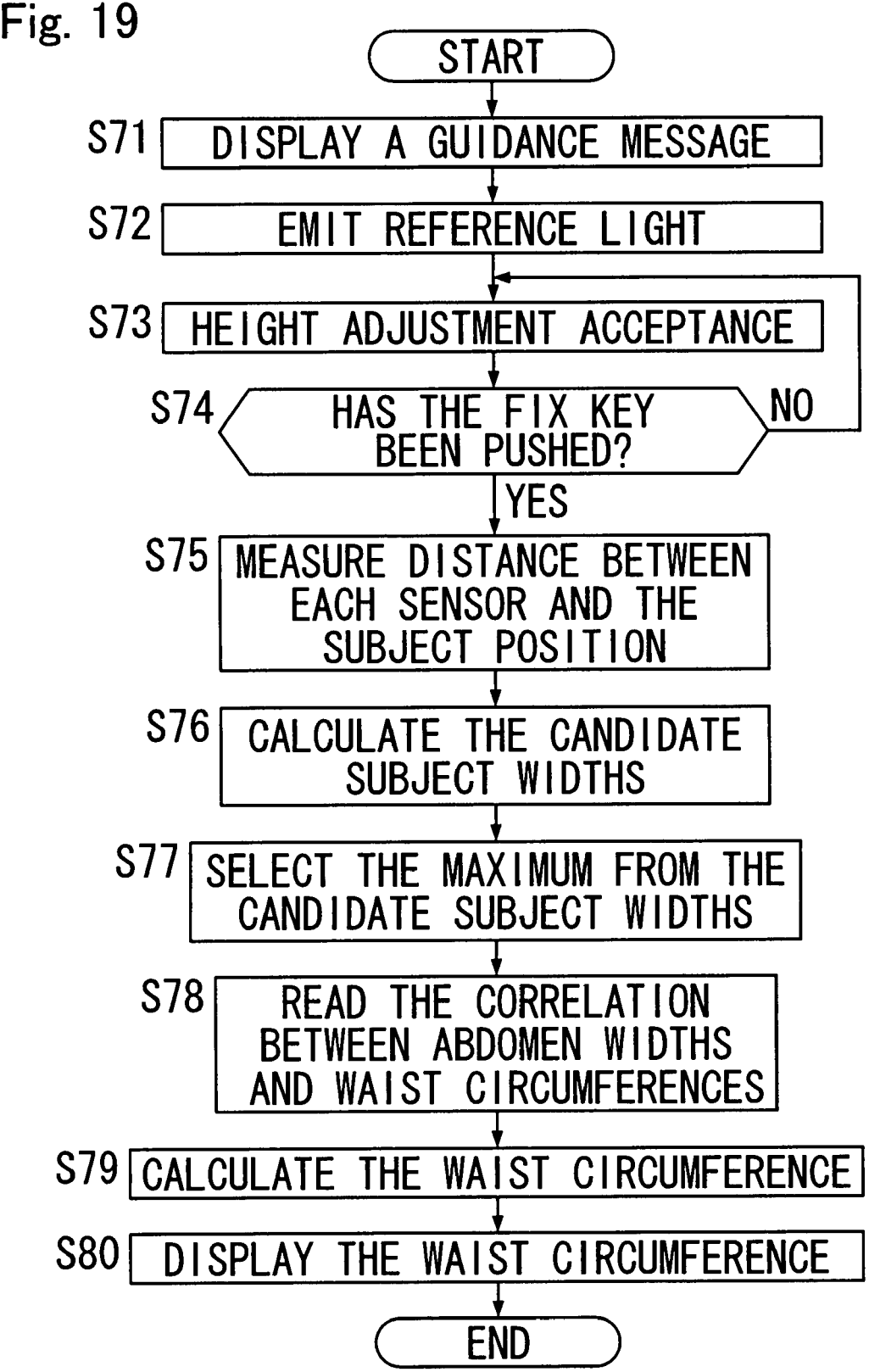
FIG. 19 is a flowchart showing use and operations of the waist circumference calculation apparatus in FIG. 15.

The operations shown in FIG. 19 are started when the ON/OFF key 221 is pushed. At step S71, the CPU 234 makes the display 204 display a guide message (e.g., "Stand on the base plate and align your toes on the reference line.") to prompt the human subject 20 to align the toes on the reference line 196 in FIG. 15.

At step S72, the CPU 234 makes the navel position indicator 218 emit the reference light. At step S73, the CPU 234 conducts a height adjustment acceptance. In the height adjustment acceptance, the CPU 234 makes the display 204 display the guide message (e.g., "Operate the Move-up key or the Move-down key so that the light is irradiated onto your navel") to prompt the human subject 20 to adjust the position of the supporting member 214. According to the guide message, the human subject 20 (or other operator) operates the Move-up key 223 or Move-down key 224 so that the reference light from the navel position indicator 218 is irradiated onto the navel N. More specifically, the CPU 234 makes the driving unit 238 raise the supporting member 214 during manipulation of the Move-up key 223, and makes the driving unit 238 lower the supporting member 214 during manipulation of the Move-down key 224.

The height adjustment acceptance ends when the Fix key 222 is pushed (step S74). After the height adjustment acceptance, the CPU 234 makes the navel position indicator 218 stop emitting and makes the display 204 show a guide message (e.g., "measurement in progress") to indicate that the measurement of the waist circumference is in progress. In addition, the CPU 234 stops the control of the driving unit 238 regardless of the manipulation of the Move-up key 223 or the Move-down key 224.

At step S75, the CPU 234 drives the sensors 26 (26a and 26b) by supplying driving command signals. In response to the command signals, each sensor 26 outputs the signal corresponding to the gap distance between the corresponding sensor 26 and the human subject 20. Each of the signals from the sensors 26 is successively selected by the selector 230 and converted by the A/D converter 232 into the digital signal. The CPU 234 stores in the memory 228 the distance data corresponding to the digital signals supplied from the A/D converter 232. Thus, the CPU 234 determines the gap distances between the sensors 26 and the human subject 20.

At steps S76 and S77, the CPU 234 serves as the abdomen width determiner for determining the abdomen width value Wsbj on the basis of the distance data stored in the memory 228. More specifically, at step S76, the CPU 234 serves as a distance calculator for calculating four candidate subject widths W1 through W4 at step S76 on the basis of the expressions (1) through (4):

$$W1 = INT - (DA1 + DB1) \quad (1)$$

$$W2 = INT - (DA2 + DB2) \quad (2)$$

$$W3 = INT - (DA3 + DB3) \quad (3)$$

$$W4 = INT - (DA4 + DB4) \quad (4)$$

At step S77, the CPU 234 serves as a maximum selector for selecting the maximum width as the abdomen width value Wsbj from among the candidate subject widths W1 through W4. As will be understood from the above description, the precision of determination of the abdomen width value Wsbj will be improved when the number of the sensors 26 is increased.

At step S78, the CPU 234 reads the regression formula (Y=aX+b) from the ROM 227 representing the correlation between abdomen width values and waist circumferences. Then, at step S79, the CPU 234 serves as the waist circumference calculator for calculating the waist circumference Y of the human subject 20 on the basis of the regression formula and the abdomen width value Wsbj (X in the regression formula) determined at step S77. At step S80, the CPU 234 makes the display 204 show the waist circumference calculated at step S79 and ends the process shown in FIG. 19.

Figure 20:
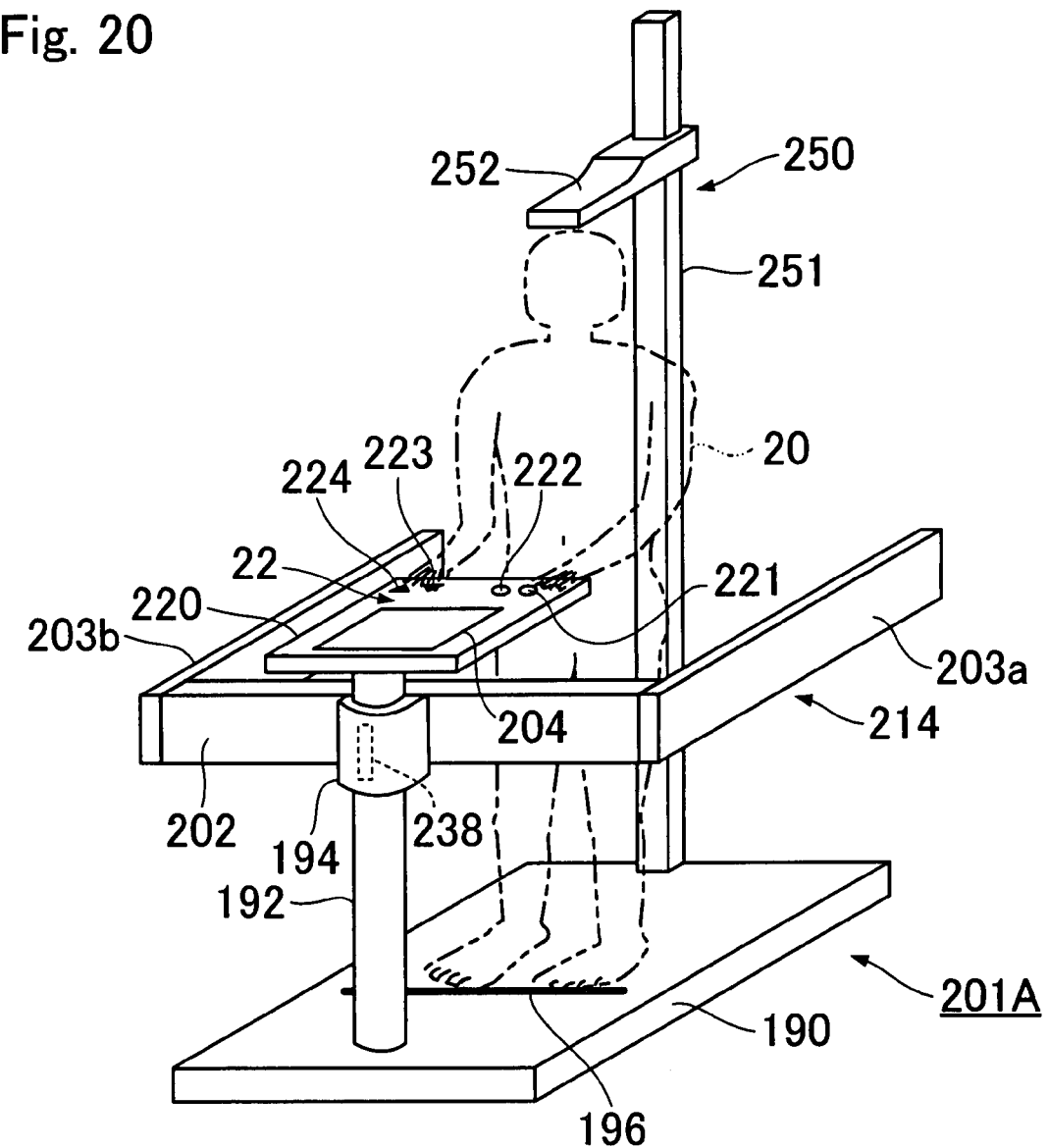
FIG. 20 is a perspective view of a waist circumference calculation apparatus according to a modification of the third embodiment.

FIG. 20 shows a modification of the above-described third embodiment. A waist circumference calculation apparatus 201A according to this modification includes a height meter 250 in addition to the third embodiment for measuring the height of the human subject 20. The height meter 250 includes a pole 251 vertically erected on the base plate 190, and a cursor 252 attached to the pole 251 so as to slide along the pole 251. The cursor 252 can move up and down in response to commands supplied from the CPU 234. The height of the cursor 252 is sent to the CPU 234 and is displayed by the display 204. According to this modification, the height of the human subject 20 standing on the base plate 190 can be measured before or after the measurement of the waist circumference.

Modifications

In the above-described first embodiment, the sensors 6a and 6b are actuated automatically by the driving mechanisms 7a and 7b that are controlled by the controller 9. In an alternative embodiment (not shown), the sensors 6a and 6b may be moved manually by the operator (e.g., human subject 20) while each sensor samples the corresponding gap distances at regular sampling distance-intervals. Similarly, in a modification of the above-described second embodiment, the sensor 6c may be moved manually by the operator.

In the above-described second and third embodiments, measurement of the bioelectrical impedance and calculation of the body composition indexes are not conducted. However, in these embodiments, the body composition indexes may be calculated in a manner similar to the first embodiment by using the electrodes 15 and electrodes supporting part 16 shown in the first embodiment. Thus, the bioelectrical impedance measuring unit (e.g., the electrodes 15) and the body composition calculator (e.g., the calculator 10) may be added to the second and third embodiments.

Although in the above-described embodiments the display (4 or 204) is used as an output device to which the measurement result is output, the apparatus may output the measurement result in any other suitable manner. For example, the apparatus may include a printer for printing out the measurement result. The apparatus may send or may store or may both send and store measurement result signals indicating the measurement result to an outside device.

In the above-described embodiments, the abdomen width value Wsbj of the human subject 20 is determined on the basis of the signals from at least one noncontact distance measuring sensor. However, means for determining the abdomen width value Wsbj is not limited to this. For example, a measuring tool, such as a vernier caliper, applied to the abdomen of the human subject 20 may be employed as the measuring unit for measuring the abdomen width value. In an alternative embodiment, the abdomen width value Wsbj measured by another device may be manually inputted into the waist circumference calculation apparatus for example via the manual interface (5 or 205). The microcomputer 8 in the first and second embodiments or the CPU 234 in the third embodiment determines the abdomen width value Wsbj on the basis of the input value. Thus, the term "determining the abdomen width value" in this specification and the appended claims includes acquiring of the input abdomen width value as well as determination of the abdomen width value based on the signals from the measuring unit.

The contact part 120 shown in FIG. 8 in the second embodiment may be disposed on the supporting member 14 of the first embodiment or the supporting member 214 of the third embodiment in the same manner as the second embodiment.

While the present invention has been particularly shown and described with reference to preferred embodiments thereof, it will be understood by those skilled in the art that various changes in form and details may be made therein without departing from the spirit and scope of the invention as defined by the claims. Such variations, alterations, and modifications are intended to be encompassed in the scope of the present invention.

What is claimed is:

1. A waist circumference calculation apparatus comprising:

an abdomen width determiner for determining an abdomen width value of a human subject;

a memory for storing a correlation between abdomen width values and waist circumferences of human beings;

a waist circumference calculator for calculating a waist circumference of the human subject on the basis of the abdomen width value determined by the abdomen width determiner and the correlation stored in the memory;

a measuring unit comprising at least one noncontact distance measuring sensor, the sensor emitting light, receiving the light reflected from whatever is in front of the sensor, and generating a signal corresponding to a distance from the sensor to whatever is in front of the sensor, wherein the abdomen width determiner determines the abdomen width value on the basis of signals generated by the sensor; and a supporting member that can be disposed in proximity to a human subject, wherein the measuring unit comprises at least one pair of the noncontact distance measuring sensors supported at the supporting member, the pair of the noncontact distance measuring sensors comprising a first sensor and a second sensor being aligned on opposite sides of the human subject within the supporting member, the first sensor measuring a first gap distance between the first sensor and a first subject position on the human subject in a first measurement line, the second sensor measuring a second gap distance between the second sensor and a second subject position on the human subject in a second measurement line parallel to or identical to the first measurement line, the measuring unit measuring a plurality of first gap distances to a plurality of first subject positions in a plurality of parallel first measurement lines and a plurality of second gap distances to a plurality of second subject positions in a plurality of parallel second measurement lines lying on a plane identical to that in which the first measurement lines lie, and wherein the abdomen width determiner further comprises:

a distance calculator for calculating a plurality of candidate subject widths on the basis of the plurality of the first gap distances and second gap distances, each candidate subject width being a distance between one of the first subject positions and one of the second subject positions; and a maximum selector for selecting a maximum subject width as the abdomen width value from among the plurality of candidate subject widths.

2. The waist circumference calculation apparatus according to claim 1, further comprising driving mechanisms for respectively moving the first sensor and second sensor with respect to the supporting member, wherein the first sensor measures a plurality of first gap distances to a plurality of first subject positions in a plurality of first parallel measurement lines, each first gap distance being between a sensor position of the first sensor and a first subject position on the human subject, and wherein the second sensor measures a plurality of second gap distances to a plurality of second subject positions in a plurality of second parallel measurement lines, each second gap distance being between a sensor position of the second sensor and a second subject position on the human subject.

3. The waist circumference calculation apparatus according to claim 1, wherein the measuring unit comprising a plurality of pairs of the noncontact distance measuring sensors, each pair comprising the first sensor and the second sensor fixedly supported at the supporting member, wherein each of the first sensors measures a first gap distance between the corresponding first sensor and a first subject position on the human subject in a first measurement line, and wherein each of the second sensors measures a second gap distance between the corresponding second sensor and a second subject position on the human subject in a second measurement line parallel to or identical to the first measurement line.

4. The waist circumference calculation apparatus according to claim 1, wherein the supporting member has a recess being of a curved shape that fits over an anterior surface of the abdomen of the human subject.

5. The waist circumference calculation apparatus according to claim 1, wherein the supporting member is a frame of a shape in which one side is open, and the supporting member can be disposed around the human subject.

6. The waist circumference calculation apparatus according to claim 1, further comprising a rod for supporting the supporting member so that the supporting member can slide along a medial line of a human subject.

7. A body composition determination apparatus comprising:

a waist circumference calculation apparatus according to claim 1;

a bioelectrical impedance measuring unit for measuring a bioelectrical impedance of the abdomen of the human subject; and a body composition calculator for calculating an index of a body composition of the human subject on the basis of the waist circumference calculated by the waist circumference calculation apparatus and the bioelectrical impedance measured by the bioelectrical impedance measuring unit.

8. A waist circumference calculation apparatus comprising:

an abdomen width determiner for determining an abdomen width value of a human subject;

a memory for storing a correlation between abdomen width values and waist circumferences of human beings;

a waist circumference calculator for calculating a waist circumference of the human subject on the basis of the abdomen width value determined by the abdomen width determiner and the correlation stored in the memory;

a measuring unit comprising at least one noncontact distance measuring sensor, the sensor emitting light, receiving the light reflected from whatever is in front of the sensor, and generating a signal corresponding to a distance from the sensor to whatever is in front of the sensor, wherein the abdomen width determiner determines the abdomen width value on the basis of signals generated by the sensor; and a supporting member that can be disposed in proximity to a human subject, wherein the at least one noncontact distance measuring sensor is supported at the supporting member, the measuring unit measuring a plurality of gap distances between the sensor and a plurality of measured positions in a plurality of measurement lines parallel to an anteroposterior direction of the human subject, and wherein the abdomen width determiner further comprises:

an end detector for detecting a first end and a second end of the human subject on the basis of an amount of each of the plurality of gap distances; and a distance calculator for calculating a distance between the first end and the second end as the abdomen width value.

9. The waist circumference calculation apparatus according to claim 8, further comprising a driving mechanism for moving the sensor with respect to the supporting member, wherein the sensor measures a plurality of gap distances to a plurality of measured positions in a plurality of parallel measurement lines.

10. The waist circumference calculation apparatus according to claim 8, wherein the measuring unit comprises a plurality of the sensors fixedly supported at the supporting member for measuring a plurality of gap distances to a plurality of measured positions in a plurality of parallel measurement lines, respectively.

11. The waist circumference calculation apparatus according to claim 8, wherein the supporting member has a recess being of a curved shape that fits over an anterior surface of the abdomen of the human subject.

12. The waist circumference calculation apparatus according to claim 8, wherein the supporting member is a frame of a shape in which one side is open, and the supporting member can be disposed around the human subject.

13. The waist circumference calculation apparatus according to claim 8, further comprising a rod for supporting the supporting member so that the supporting member can slide along a medial line of a human subject.

14. A body composition determination apparatus comprising:

a waist circumference calculation apparatus according to claim 8;

a bioelectrical impedance measuring unit for measuring a bioelectrical impedance of the abdomen of the human subject; and a body composition calculator for calculating an index of a body composition of the human subject on the basis of the waist circumference calculated by the waist circumference calculation apparatus and the bioelectrical impedance measured by the bioelectrical impedance measuring unit.

15. A waist circumference calculation apparatus comprising:

an abdomen width determiner for determining an abdomen width value of a human subject;

a memory for storing a correlation between abdomen width values and waist circumferences of human beings;

a waist circumference calculator for calculating a waist circumference of the human subject on the basis of the abdomen width value determined by the abdomen width determiner and the correlation stored in the memory, wherein the correlation is expressed by the following regression formula:

$$Y=aX+b$$

where "Y" is a waist circumference of a human being, "X" is an abdomen width value of a human being, and "a" and "b" are constants; and a measuring unit comprising at least one noncontact distance measuring sensor, the sensor emitting light, receiving the light reflected from whatever is in front of the sensor, and generating a signal corresponding to a distance from the sensor to whatever is in front of the sensor, wherein the abdomen width determiner determines the abdomen width value on the basis of signals generated by the sensor.

16. A waist circumference calculation apparatus comprising:

an abdomen width determiner for determining an abdomen width value of a human subject;

a memory for storing a correlation between abdomen width values and waist circumferences of human beings;

a waist circumference calculator for calculating a waist circumference of the human subject on the basis of the abdomen width value determined by the abdomen width determiner and the correlation stored in the memory;

a navel position indicator disposed at the supporting member for indicating a reference position at which a navel of the human subject would be located; and a measuring unit comprising at least one noncontact distance measuring sensor, the sensor emitting light, receiving the light reflected from whatever is in front of the sensor, and generating a signal corresponding to a distance from the sensor to whatever is in front of the sensor, wherein the abdomen width determiner determines the abdomen width value on the basis of signals generated by the sensor.

* * * * *